(12) United States Patent
Jain et al.

(10) Patent No.: US 11,793,809 B2
(45) Date of Patent: *Oct. 24, 2023

(54) PHARMACEUTICAL COMPOSITIONS OF NILOTINIB

(71) Applicant: SLAYBACK PHARMA LLC, Princeton, NJ (US)

(72) Inventors: Paras P. Jain, Maharashtra (IN); Ajay Kumar Singh, Princeton, NJ (US); Keerthi Priya, Telangana (IN); Girish Kumar Jain, Maharashtra (IN); Girish G. Kore, Maharashtra (IN); Sandeep Jain, Madhya Pradesh (IN); Hanimi Reddy Bapatu, Telangana (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 270 days.

This patent is subject to a terminal disclaimer.

(21) Appl. No.: 16/953,728

(22) Filed: Nov. 20, 2020

(65) Prior Publication Data

US 2021/0077485 A1  Mar. 18, 2021

Related U.S. Application Data

(63) Continuation of application No. 16/793,833, filed on Feb. 18, 2020, now Pat. No. 10,874,671.

(30) Foreign Application Priority Data

Feb. 18, 2019  (IN) .............................. 201941006393

(51) Int. Cl.
*A61K 31/4985* (2006.01)
*A61K 9/20* (2006.01)
*A61K 9/10* (2006.01)

(52) U.S. Cl.
CPC ............ *A61K 31/4985* (2013.01); *A61K 9/10* (2013.01); *A61K 9/2095* (2013.01)

(58) Field of Classification Search
CPC .................................................. A61K 31/4985
See application file for complete search history.

(56) References Cited

U.S. PATENT DOCUMENTS

| | | | |
|---|---|---|---|
| 8,641,948 B2 | 2/2014 | Ghogh et al. | |
| 8,937,082 B2 | 1/2015 | Piran et al. | |
| 9,090,598 B2 | 7/2015 | Piran et al. | |
| 9,301,957 B2 | 4/2016 | Bhardwaj et al. | |
| 10,143,683 B2 | 12/2018 | Brisander et al. | |
| 10,874,671 B2 * | 12/2020 | Jain .................... | A61K 9/2027 |
| 2014/0038994 A1 | 2/2014 | Manley et al. | |
| 2014/0356443 A1 | 12/2014 | Brisander et al. | |
| 2015/0273070 A1 | 10/2015 | Li et al. | |
| 2019/0071426 A1 | 3/2019 | Ceric et al. | |

FOREIGN PATENT DOCUMENTS

| | | |
|---|---|---|
| EP | 2 742 940 A1 | 6/2014 |
| JP | 2014-517040 A | 7/2014 |
| JP | 2018-172393 A | 11/2018 |
| WO | WO 2012/174082 A1 | 12/2012 |
| WO | WO 2016/016665 A1 | 2/2016 |
| WO | WO 2017/149550 A1 | 9/2017 |
| WO | WO 2017/160703 A1 | 9/2017 |

OTHER PUBLICATIONS

Extended European Search Report for European Application No. 20760325.9, dated Feb. 24, 2022.
Japanese Decision of Rejection for Japanese Application No. 2021-548238, dated Jun. 7, 2022, with English translation.
"Highlights of Prescribing Information," for TASIGNA® nilotinib oral capsules, Approved by U.S. Food and Drug Administration, Revised Sep. 2019.
Herbrink, M., et al, "Improving the solubility of nilotinib through novel spray-dried solid dispersions," International Journal of Pharmaceutics, Aug. 30, 2017, vol. 529, Nos. 1-2, pp. 294-302.
International Search Report and the Written Opinion of the International Searching Authority, dated Apr. 28, 2020, for International Application PCT/US2020/018564.
Jesson, G., et al, "Carbon Dioxide-Mediated Generation of Hybrid Nanoparticles for Improved Bioavailability of Protein Kinase Inhibitors," Pharm Res, 2014, vol. 31, pp. 694-705.
Chinese Office Action and Search Report for Chinese Application No. 202080021471.4, dated Mar. 4, 2022, with English translation.
Japanese Office Action for Japanese Application No. 2021-548238, dated Jan. 18, 2022, with English translation.
European Office Action for Appl. No. 20 760 325.9 dated Dec. 22, 2022.

* cited by examiner

*Primary Examiner* — Rei Tsang Shiao
(74) *Attorney, Agent, or Firm* — Birch, Stewart, Kolasch & Birch, LLP

(57) ABSTRACT

Amorphous solid dispersions of nilotinib fumarate or nilotinib tartrate are provided, as well as pharmaceutical compositions thereof, wherein the compositions exhibit enhanced bioavailability in the fasted state. Preferably, the compositions may be orally administered to a patient in either the fed or fasted state, with a decrease or elimination of the food effect. Preferably, following oral administration of the pharmaceutical compositions, there is no substantial difference in the pharmacokinetic parameters (e.g., $C_{max}$, $AUC_{0-t}$ and/or $AUC_{0-infinity}$) of nilotinib, regardless of whether the pharmaceutical compositions are administered to a subject in the fed or fasted state.

9 Claims, 9 Drawing Sheets

PHARMACEUTICAL COMPOSITIONS OF NILOTINIB

CROSS-REFERENCE TO RELATED APPLICATIONS

This application is a Continuation of copending application Ser. No. 16/793,833 filed on Feb. 18, 2020, which claims foreign priority to Indian Application No. IN 201941006393, filed on Feb. 18, 2019, which is incorporated by reference in its entirety.

FIELD OF THE INVENTION

Amorphous solid dispersions of nilotinib fumarate or nilotinib tartrate are provided, as well as pharmaceutical compositions thereof, wherein the inventive compositions exhibit enhanced bioavailability in the fasted state compared to a reference formulation. Preferably, the pharmaceutical compositions eliminate or reduce the food effect, such that they may be administered without regard to food. The composition may preferably comprise a granulate material that can be filled into a capsule or compressed into a tablet.

The present application also provides methods for treating proliferation disorders in a human subject, such as chronic myeloid leukemia and gastrointestinal stromal tumours, by administering a pharmaceutically effective amount of the pharmaceutical composition.

BACKGROUND OF THE INVENTION

Nilotinib is chemically described as 4-methyl-N-[3-(4-methyl-1H-imidazol-1-yl)-5-(trifluoromethyl) phenyl]-3-[[4-(3-pyridinyl)-2-pyrimidinyl] amino]-benzamide and is an inhibitor of protein tyrosine kinase (TK), and in particular, it is a selective inhibitor of Bcr-Abl tyrosine kinase. Examples of conditions that may be treated by nilotinib include, but are not limited to, chronic myeloid leukemia and gastrointestinal stromal tumours.

Nilotinib is characterized as a Biopharmaceutical Classification System (BCS) class IV compound, which means that it has low/moderate aqueous solubility and low permeability. The solubility of nilotinib at 25° C. in aqueous solutions decreases strongly with increasing pH and it is practically insoluble at pH 4.5 and higher. This decrease in the solubility of nilotinib in environments with a pH of more than 1.0 leads to a decrease in the absorption of nilotinib. Nilotinib hydrochloride is poorly water soluble and hence, it would be difficult to formulate and deliver oral dosage forms which exhibit good bioavailability.

Nilotinib is currently marketed under the brand name TASIGNA®. TASIGNA® is available in the form of hard gelatin capsules containing nilotinib hydrochloride monohydrate equivalent to 50 mg, 150 mg and 200 mg of nilotinib. The package insert of TASIGNA® reveals that the patients are instructed to take the capsules twice daily at approximately 12-hour intervals. TASIGNA® is prescribed as 300 mg twice daily (600 mg total daily dose) for treatment of newly diagnosed philadelphia chromosome positive chronic myeloid leukemia and 400 mg twice daily (800 mg total daily dose) for treatment resistant or intolerant philadelphia chromosome positive chronic myelogenous leukemia.

The bioavailability of TASIGNA® is increased when given with a meal. Compared to the fasted state, the systemic exposure (AUC) is reported to increase by 82% when the dose is given 30 minutes after a high fat meal. In order to minimize the food effect, the label indicates that it is necessary to administer the capsules on an empty stomach. Therefore, no food should be consumed for at least 2 hours before the dose is taken and for at least 1 hour after the dose is taken.

Commercially available preparations of nilotinib pose risk of adverse effects, particularly if the patient ingests the tablets of nilotinib with or after meals, particularly high fat meals, because the rate and extent of absorption (area under the plasma profile curve and the $C_{max}$) are increased by 82% and 112%, respectively. (Castagnetti et al; Hematology Meeting Reports, 2008; 2 (5); 22-26).

It is desirable to have a composition for oral administration which provides nilotinib to a patient population with lower variability in bioavailability, thus providing consistent PK parameters (e.g., a narrower observed range for $C_{max}$ and AUC values) across patient population to whom the formulation is administered.

Moreover, it is also desirable to have a composition for oral administration which provides enhanced nilotinib bioavailability compared to commercially available formulation, i.e., TASIGNA®, thus yielding higher plasma levels in fasted state.

In addition, it is also desirable to have a composition for oral administration which provides an acceptable plasma level of nilotinib when administered to a patient in fed state.

Thus, what is needed is a nilotinib composition that is suitable for oral administration to patients, and which provides uniform plasma level(s) and sufficient nilotinib exposure (AUC) in fasted and fed states. What is also needed is a nilotinib oral composition which exhibit less variability in pharmacokinetic parameters (e.g., $C_{max}$, $AUC_{0-t}$ and $AUC_{0-infinity}$) than commercially available nilotinib formulation (TASIGNA®).

There exists a need for nilotinib oral compositions which exhibit improved bioavailability in fasting state and also exhibit less variability in pharmacokinetic parameters (e.g., $C_{max}$, $AUC_{0-t}$ and $AUC_{0-infinity}$) in fasted and fed states, than a reference product, i.e. commercially available nilotinib formulation (TASIGNA®). There also exists a need for administering reduced daily doses of nilotinib, wherein the compositions exhibit enhanced bioavailability in fasted state and can be administered without regard to food.

Furthermore, solid dispersions of poorly soluble drugs in polymers are generally unstable overtime. Amorphous solid dispersions especially tend to convert to crystalline forms over time, which can lead to improper dosing due to differences of the bioavailability and solubility of crystalline drug material compared to amorphous drug material. One skilled in the art cannot predict which carriers, if any, would be useful for preparing stable amorphous dispersions for a particular drug product.

Hence, there exists a need to provide compositions suitable for oral administration comprising stable amorphous solid dispersions of nilotinib or its pharmaceutically acceptable salts, wherein the compositions exhibit enhanced bioavailability in the fasted state, and which can be administered without regard to food.

SUMMARY OF THE INVENTION

The present invention relates to pharmaceutical compositions comprising amorphous solid dispersion of nilotinib or pharmaceutically acceptable salts thereof (e.g., nilotinib fumarate or nilotinib tartrate) for oral administration, wherein the composition exhibits enhanced bioavailability in the fasted state and may be administered without regard to food.

The present application provides pharmaceutical compositions of nilotinib or its pharmaceutically acceptable salts thereof (e.g., nilotinib fumarate or nilotinib tartrate), of reduced strength/dose as compared to the dose of reference formulation, wherein the composition eliminates or reduces the food effect.

In an embodiment, the dose of nilotinib administered to a human subject is reduced by at least 10% in comparison to a reference formulation which is current marketed formulation of nilotinib (i.e., TASIGNA®). In yet another embodiment, the dose of nilotinib administered to a human subject is reduced by at least 50% in comparison to a reference formulation which is current marketed formulation of nilotinib (i.e., TASIGNA®).

The present application further provides pharmaceutical compositions of nilotinib exhibiting a mean $C_{max}$ and AUC underfasting condition which is at least about 2 to 2.5 times higher than the mean $C_{max}$ and AUC of TASIGNA® under fasting condition.

The present application further provides pharmaceutical compositions of nilotinib fumarate or nilotinib tartrate having enhanced bioavailability in comparison to the current marketed formulation of nilotinib (i.e., TASIGNA®) in fasted state and still be bioequivalent to TASIGNA® underfed and fasting conditions.

Solid dispersions, methods of making solid dispersions, methods of making pharmaceutical compositions, and methods of treatment using the pharmaceutical compositions described are also provided.

The present application provides amorphous solid dispersions comprising nilotinib fumarate or nilotinib tartrate. Pharmaceutical compositions are also provided, which comprise an effective amount of amorphous solid dispersion of nilotinib fumarate or nilotinib tartrate, wherein the solid dispersion comprises a pharmaceutically acceptable carrier and optionally at least one organic acid, and wherein the pharmaceutical composition provides enhanced bioavailability when compared to a reference formulation in fasted state.

The pharmaceutical compositions preferably comprise an effective amount of amorphous solid dispersion of nilotinib fumarate or nilotinib tartrate, wherein the solid dispersion further comprises a pharmaceutically acceptable carrier and optionally at least one organic acid, and wherein at least one pharmacokinetic parameter of nilotinib in a human subject subsequent to administration in the fasted state is from about 80% to about 125% of that pharmacokinetic parameter of nilotinib in a human subject subsequent to administration in the fed state, wherein at least one pharmacokinetic parameter is selected from $AUC_{0-infinity}$, $C_{max}$, $AUC_{0-t}$, or combinations thereof.

Each of embodiments described in this application may further have one or more of the following additional elements in any combination:

Element 1: the amorphous solid dispersions may further comprise a pharmaceutically acceptable carrier, and optionally, at least one organic acid.

Element 2: the amorphous solid dispersions may be prepared by hot-melt extrusion, spray-drying or co-precipitation.

Element 3: the amorphous solid dispersions may have a weight ratio of the nilotinib fumarate or the nilotinib tartrate, respectively, to the pharmaceutically acceptable carrier from about 1:1 to about 1:6, preferably from about 1:3 to about 1:4.

Element 4: the amorphous solid dispersions may comprise, consist essentially of or consist of a pharmaceutically acceptable carrier selected from the group consisting of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and mixtures thereof.

Element 5: the amorphous solid dispersions may optionally contain an organic acid, and the organic acid may be selected from the group consisting of acetic acid, propionic acid, octanoic acid, decanoic acid, dodecanoic acid, glycolic acid, lactic acid, fumaric acid, succinic acid, adipic acid, pimelic acid, malic acid, tartaric acid, citric acid, glutamic acid, aspartic acid, maleic acid, benzoic acid, salicylic acid, phthalic acid, phenylacetic acid, cinnamic acid, ascorbic acid, and mixtures thereof.

Element 6: the amorphous solid dispersions may have nilotinib fumarate or the nilotinib tartrate present in a weight ratio relative to the organic acid of about 1:0.5 to about 1:5, preferably present in a ratio of about 1:2, more preferably present in a ratio of about 1:1.

Element 7: the amorphous solid dispersions may further comprise one or more pharmaceutically acceptable excipients selected from the group consisting of diluents, binders, disintegrants, lubricants, glidants, surfactants, solubilizers, plasticizers, stabilizing agents, antioxidants and combinations thereof.

Element 8: the pharmaceutical compositions may comprise from about 25 mg to about 200 mg of nilotinib fumarate or nilotinib tartrate.

Element 9: the pharmaceutical compositions may preferably be in the form of a tablet, a capsule, a caplet, beads, granules or oral suspension.

Element 10: the pharmaceutical compositions may further comprise one or more pharmaceutically acceptable excipients selected from the group consisting of diluents, binders, disintegrants, lubricants, glidants, surfactants, plasticizers, solubilizers, stabilizing agents, antioxidants and combinations thereof.

Element 11: the pharmaceutical compositions may preferably be obtained by direct compression, wet granulation or dry granulation.

Element 12: the pharmaceutical compositions may preferably be in the form of a tablet comprising: (a) an amorphous solid dispersion of nilotinib fumarate or nilotinib tartrate, for example, in the form of granules, (b) at least one intra-granular excipient, (c) at least one extra-granular excipient, and (d) optionally, a coating.

Element 13: the solid dispersions or pharmaceutical compositions may preferably remain stable under accelerated conditions, e.g., the compositions remain stable for at least 6 months at 40° C./75% RH ("relative humidity") or 25° C./60% RH ("relative humidity").

Element 14: the solid dispersions or pharmaceutical compositions preferably have a level of any unknown impurity that is less than about 0.2% (w/w), preferably less than about 0.15% (w/w), and more preferably less than about 0.1% (w/w) as measured by HPLC.

Element 15: the solid dispersions and pharmaceutical compositions may preferably be made by (a) dry-blending nilotinib fumarate or nilotinib tartrate and at least one pharmaceutically acceptable carrier selected from the group consisting of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and combinations thereof, to form a mixture; (b) heating the mixture to a temperature sufficient to form a molten dispersion, wherein the melting is carried out under a temperature from 80° C. to 200° C. and a screw speed from 30 to 1000 rpm; and (c) extruding the molten dispersion to provide a composition comprising a solid dispersion of nilotinib in at least one pharmaceutically acceptable carrier. The process may further comprise the steps of: (d) milling the composition from (c) to provide granules comprising nilotinib fumarate or nilotinib tartrate; (e) mixing the granules from (d) with an extra-granular mixture comprising one or more excipients selected from the group consisting of crospovidone, colloidal silica, magnesium stearate, and mixtures thereof, to provide a blend; (f) compressing the blend into tablets or filling the blend into a capsule shell; and (g) optionally, coating the tablets or capsule shell.

Element 16: the solid dispersions and pharmaceutical compositions may preferably be included in a kit comprising: (a) a pharmaceutical composition according to the invention; and (b) instructions for oral administration of the composition, wherein the instructions indicate that the composition can be administered to a human subject without regard to food.

Element 17: the solid dispersions and pharmaceutical compositions may preferably be used in a method for treating a proliferative disorder in a human subject, which method comprises: (a) providing a pharmaceutical composition; and (b) providing instructions for oral administration of the composition indicating that the composition can be administered to a human subject without regard to food.

By way of non-limiting example, exemplary combinations applicable to the embodiments described in this application may include any combination with one or more of the elements described above.

DETAILED DESCRIPTION OF THE INVENTION

Figure 1:
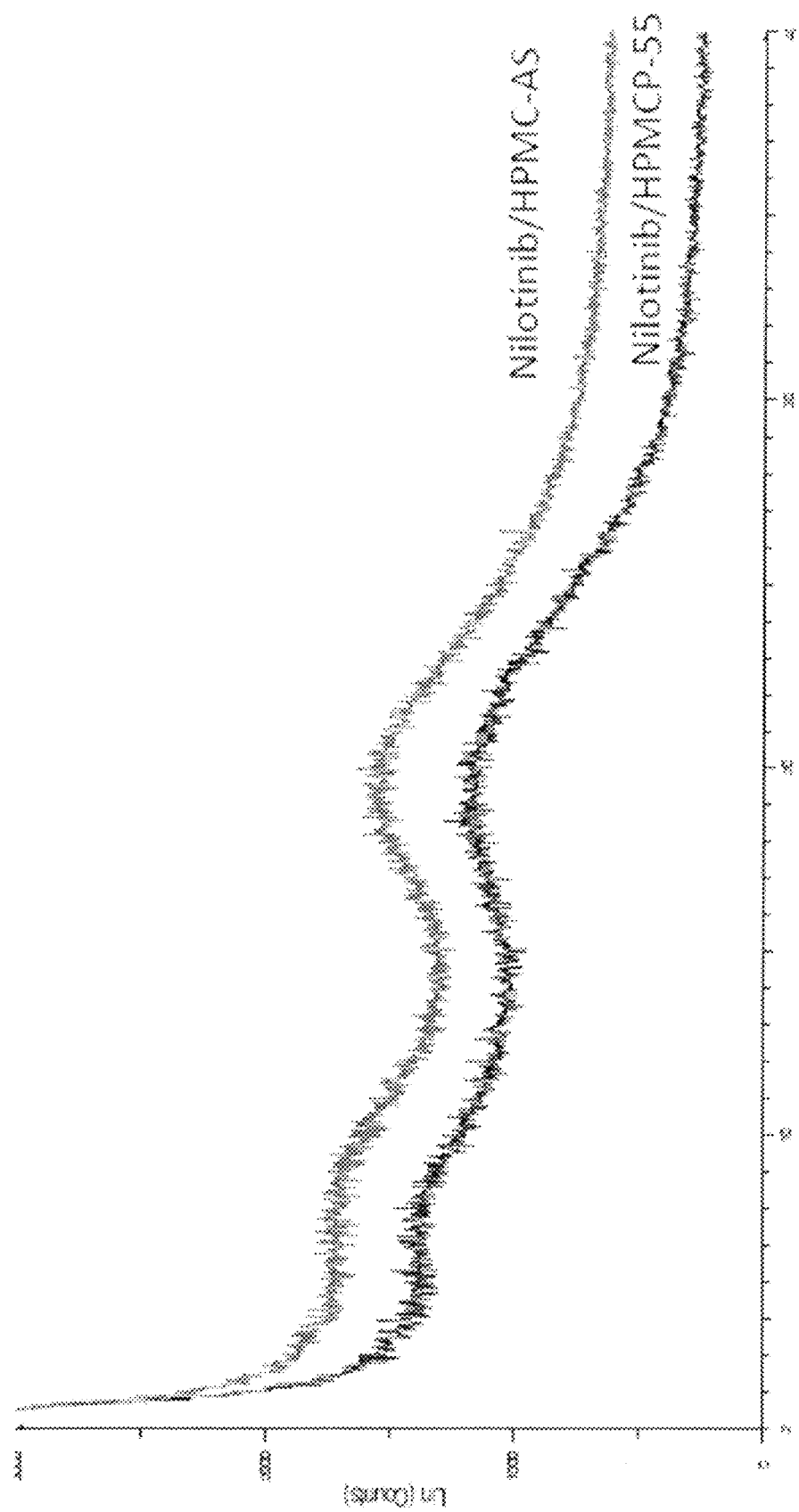
FIG. 1 illustrates powder X-ray diffraction patterns of composition 2 and 5 from Example 1.

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

The terms "about" and "approximate," when used along with a numerical variable, generally means the value of the variable and all the values of the variable within a measurement or an experimental error (e.g., 95% confidence interval for the mean) or within a specified value (e.g., ±10%) within a broader range.

As used herein the term "nilotinib" refers to nilotinib free base or its pharmaceutically acceptable salts, solvates or hydrates thereof. In principle, any crystalline form of nilotinib or amorphous form of nilotinib may be used for manufacturing the pharmaceutical composition of the present invention.

The term "pharmaceutically acceptable" substances means those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to nilotinib salts which are formed with inorganic acids or organic acids. Suitable salts include salts formed with organic acids such as citric acid, tartaric acid, or fumaric acid.

The terms "pharmaceutical composition," "pharmaceutical product," "pharmaceutical dosage form," "dosage form," "pharmaceutical formulation," etc., refer to a pharmaceutical composition administered to a patient in need of treatment, which is typically in the form of powder, granules, pill, beads, capsule, caplet, tablet, oral suspension etc.

The terms "carrier" and "pharmaceutically acceptable carrier" are interchangeable. The carrier is able to form a matrix embedding (surrounding) the active ingredient. The matrix may comprise one carrier or a mixture of two or more carriers. The carrier used in the solid dispersion of the present invention may be an enteric polymer or non-enteric polymer.

According to the embodiments of the invention, the pharmaceutically acceptable carrier is selected from one or more of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), and polyvinyl pyrrolidine (PVP).

According to the embodiments of the invention, the hydroxypropyl methylcellulose acetate succinate (HPMC- AS) comprises various types, such as LF, LG, MF, MG, HF and HG, etc., the first letters L, M and H of the type's names mean the pH level at the beginning of dissolution of HPMC-AS. For example, L refers to low level (e.g., HPMC-AS begins to be dissolved when the pH value is more than 5.5), M refers to middle level (e.g., HPMC-AS begins to be dissolved when the pH value is more than 6.0), H refers to high level (e.g., HPMC-AS begins to be dissolved when the pH value is more than 6.5). The second letters F and G refer to the particle size of HPMC-AS, where F refers to fine powder, and G refers to granular. In some embodiments, the type of HPMC-AS is LF; in some embodiments, the type of HPMC-AS is MF; in some embodiments, the type of HPMC-AS is HG.

By "solid dispersion" is meant a molecular dispersion of a compound, particularly a drug substance within a carrier. The term solid dispersion in general means a system in solid state comprising at least two components, wherein one component is dispersed substantially evenly throughout the other component(s). For example, solid dispersions may be the dispersion of one or more active ingredients in an inert carrier or matrix at solid state, prepared by the melting, solvent, or melting-solvent methods. While not wishing to be bound by theory, in a solid dispersion, the drug may be present in a molecular state, colloidal state, metastable state, or an amorphous state. Formation of a molecular dispersion may provide a means of reducing the particle size to nearly molecular levels (i.e., there are no particles).

The term "solubility" means solubility of nilotinib or its pharmaceutically acceptable salts in aqueous media such as water, buffer, gastrointestinal simulated fluid, gastrointestinal fluid and the like.

The term "in vivo" in general means in the living body of a plant or animal, whereas the term "in vitro" generally means outside the body and in an artificial environment.

As used herein, the term "reference formulation" is a formulation that is used for comparison. Preferably, the reference formulation may refer to an oral dosage form containing 50 mg, 150 mg or 200 mg of nilotinib hydrochloride. Preferably, the reference formulation corresponds to an oral dosage form of nilotinib, which is currently marketed under the brand name TASIGNA®.

The term "subject" refers to an animal, including a human or non-human (e.g., beagle dogs). The terms patient and subject may be used interchangeably herein.

Enhanced Bioavailability and Reduced/Eliminated Food Effect

The term "bioavailability" indicates the extent to which a drug or another substance is utilized by a target tissue after administration. For example, "bioavailability" may refer to the fraction of drug absorbed following administration to a subject or patient underfed or fasted state. In certain aspects, under fasted state, the bioavailability of nilotinib when formulated as described herein is at least about 15%, but may be greater than 20%, 25%, 30%, 35%, 40%, 45%, or 50% of the dose administered.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0\text{-}infinity}$" means the area under a plasma drug concentration-time curve from time point of 0 to infinity after drug administration, and the term "$AUC_{0\text{-}t}$" means the area under a plasma drug concentration-time curve from time point of 0 to t after drug administration.

As used herein, the term "enhanced bioavailability" refers to increase in concentration of the active ingredient in the body fluid provided by the compositions of the present invention when compared to concentration of the active ingredient in the body fluid obtained from a reference formulation under identical conditions. In certain aspects, under fasted state, the bioavailability of nilotinib when formulated as described herein is enhanced at least about 15%, but may be greater than 20%, 25%, 30%, 35%, 40%, 45%, or 50% of the dose administered when compared to a reference formulation under identical conditions.

Reference throughout this specification will be made to the administration of a pharmaceutical composition under fed conditions or fasted conditions. It is well understood in the art that the pharmacokinetic performance of some compositions is affected by the presence or absence of food in the gastro-intestinal system. These references thus relate to the normally accepted administration circumstances that are referred to in the art as "fed" or "fasted."

As used herein, the term "fasted state" means that the human or other mammal has not ingested 500 calories or more than 500 calories for at least two hours before taking nilotinib solid oral dosage form and for at least two hours after taking nilotinib solid oral dosage form.

As used herein, the term "fed state" refers to a human who has eaten a United States Food and Drug Administration (FDA) standard high fat breakfast (or other meal containing a comparable quantity of fat and calories) within said time period. The meal is high in both fat (approximately 50% of total calorie content of the meal) and calories (approximately 800-1000 calories).

The term "food effect" as used herein means food-drug interactions which either decrease or increase the extent of drug absorption. In other words the bioavailability for a drug is altered when administered under fasted state, in comparison to the drug when administered in the fed state. It may refer to a relative difference in one or more of $AUC_\infty$, $AUC_{0\text{-}t}$ and/or $C_{max}$ of a drug, when said drug or a formulation thereof is administered orally to a human, concomitantly with food or in a fed state as compared to the same values when the same formulation is administered in a fasted state or without food.

In certain aspects, the food effect may be defined as the ratio of the $C_{max}$ and/or AUC values of the tested drug in fed versus fasted states. Measuring the $C_{max}$ and/or AUC values of the tested drug in fed and in fasted states is standard practice in the art. Reduction of food effect can be determined by comparing the value of the ratio from the composition or pharmaceutical composition of the invention and the value of a composition without the solubilized form disclosed in the present invention.

In certain aspects, the pharmaceutical compositions described herein reduce or eliminate the food effect. As used herein, "reducing the food effect" refers to narrowing the difference in bioavailability, e.g., $AUC_\infty$, $AUC_{0\text{-}t}$ and/or $C_{max}$ for a drug administered under fasted states in comparison to the drug administered under fed states. In certain aspects, the food effect is eliminated. Thus, upon oral administration of a pharmaceutical composition as described herein, to a mammal in need thereof, there is not a significant food effect. In other words, the difference between a pharmacokinetic parameter measured after oral administration to a mammal with and without food, respectively, is less than 40%, e.g., less than 35%, less than 30%, less than 25%, less than 20%, less than 15%, less than 10 or less than 5%. Preferably the composition or the pharmaceutical composition of the invention has at least 15% reduced food effect, preferably 20%, preferably 25%, preferably 30%, preferably 40%, reduced food effect.

Pharmacokinetic parameters for the compositions can be measured in a single or multiple dose study using a replicate or a non-replicate design. For example, the pharmacokinetic parameters can be measured in a single dose pharmacokinetic study using a two-period, two-sequence crossover design. Alternately, a four-period, replicate design crossover study may also be used. Pharmacokinetic parameters characterizing rate and extent of nilotinib absorption are evaluated statistically. The area under the plasma concentration-time curve from time zero to the time of measurement of the last quantifiable concentration ($AUC_{0-t}$) and to infinity ($AUC_{0-infinity}$), $C_{max}$, and $T_{max}$ can be determined according to standard techniques. Statistical analysis of pharmacokinetic data is performed on logarithmic transformed data (e.g., $AUC_{0-t}$, $AUC_{0-infinity}$, or $C_{max}$ data) using analysis of variance (ANOVA).

The difference in AUC of the compositions of the present invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some aspects, following administration of the pharmaceutical composition to subjects (e.g., fed subjects or fasted subjects), the mean bioavailability is greater than about 20% (e.g., greater than 25%, 30%, 35%, 40%, 45%, 50%, 55%, 60%, 65%, 70%, 75%, 80%, 85%, 90%, 95%, or even 99%) or between about 20% to about 90% (e.g., from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%).

In some aspects, the ratio of the mean bioavailability for fed subjects to the mean bioavailability for fasted subjects is from about 1.0 to about 2.0 (e.g., from 1.0 to 1.1, from 1.0 to 1.2, from 1.0 to 1.3, from 1.0 to 1.4, from 1.0 to 1.5, from 1.0 to 1.6, from 1.0 to 1.7, from 1.0 to 1.8, from 1.0 to 1.9, from 1.3 to 1.4, from 1.3 to 1.5, from 1.3 to 1.6, from 1.3 to 1.7, from 1.3 to 1.8, from 1.3 to 1.9, from 1.3 to 2.0, from 1.5 to 1.6, from 1.5 to 1.7, from 1.5 to 1.8, from 1.5 to 1.9, from 1.5 to 2.0, from 1.7 to 1.8, from 1.7 to 1.9, from 1.7 to 2.0, from 1.8 to 1.9, and from 1.8 to 2.0).

In some aspects, administration of the pharmaceutical composition to fed and fasted subjects produces a coefficient of variation in $AUC_{0-t}$, $T_{max}$, $C_{max}$ and/or $AUC_{\infty}$ of less than about 60% (e.g., less than 55%, 50%, 45%, 40%, 35%, 30%, 25%, 20%, and 15%). In particular embodiments, the coefficient of variation in $C_{max}$ and/or $AUC_{\infty}$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

In some aspects, administration of the pharmaceutical composition to a fasted subject produces mean $C_{max}$ that is greater than about 100 ng/mL (e.g., greater than about 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, and/or up to about 1000 ng/mL) for a 50 mg equivalent dose of nilotinib.

In some aspects, administration of the pharmaceutical composition to a fasted subject produces mean $AUC_{0-\infty}$ that is greater than about 1500 hr*ng/mL (e.g., greater than 1500 hr*ng/mL, 1600 hr*ng/mL, 1700 hr*ng/mL, 1800 hr*ng/mL, 1900 hr*ng/mL, 2000 hr*ng/mL, 2100 hr*ng/mL, 2200 hr*ng/mL, 2300 hr*ng/mL, 2400 hr*ng/mL, 2500 hr*ng/mL, 2600 hr*ng/mL, 2700 hr*ng/mL, 2800 hr*ng/mL, 2900 hr*ng/mL and/or greater than about 3000 hr*ng/mL) for a 50 mg equivalent dose of nilotinib.

Pharmaceutically Acceptable Salts of Nilotinib

Pharmaceutically acceptable salts of nilotinib may be formed as acid addition salts, for example with organic or inorganic acids.

Suitable inorganic acids include, but are not limited to, halogen acids, such as hydrochloric acid, sulfuric acid, or phosphoric acid.

Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, malic acid, tartaric acid, citric acid, amino acids, such as glutamic acid or aspartic acid, maleic acid, benzoic acid, salicylic acid, cinnamic acid, or other organic protonic acids, such as ascorbic acid. Useful salts of nilotinib for preparing inventive compositions herein are nilotinib tartrate and nilotinib fumarate.

Solid Dispersions of Nilotinib

The term "solid dispersion" refers to a system in a solid-state comprising at least two components, wherein one component is dispersed throughout the other component or components.

The solid dispersions of nilotinib may be formed by any conventional technique, e.g., spray drying, co-grinding, hot melt extrusion, freeze drying, rotary evaporation, solvent evaporation, co-precipitation, lyophilization, or any suitable solvent removal process. In an embodiment, solid dispersions of nilotinib of the present application comprises crystalline and/or amorphous forms of nilotinib free base or a pharmaceutically acceptable salt thereof, and a pharmaceutically acceptable carrier.

The nilotinib starting material used in the process for preparation of the solid dispersion may be crystalline or amorphous form. Alternatively, it may be obtained in situ from a previous processing step.

The nilotinib in the solid dispersion obtained may be present in either crystalline or amorphous form.

A solid that is in the "amorphous" solid state form means that it is in a non-crystalline state. Amorphous solids generally possess crystal-like short-range molecular arrangement, but no long-range order of molecular packing as are found in crystalline solids. The solid-state form of a solid, such as the drug substance in the amorphous dispersion, may be determined by Polarized Light Microscopy, X-Ray Powder Diffraction (XPRD), Differential Scanning Calorimetry (DSC), or other standard techniques known to those of skill in the art. Preferably, the amorphous solid contains drug substance in a substantially amorphous solid-state form, e.g., at least about 80% of the drug substance in the dispersion is in an amorphous form, more preferably at least about 90% of the drug substance in the dispersion is in an amorphous form, and most preferably at least about 95% of the drug substance in the dispersion is in amorphous form.

In some embodiments, at least about 90% (e.g., at least 95%, 96%, 97%, 98%, 99%, 99.5%, or even 99.9%, such as from 90% to 99.9%, from 90% to 99.5%, from 90% to 99%, from 90% to 98%, from 90% to 97%, from 90% to 96%, from 90% to 95%, from 95% to 99.9%, from 95% to 99.5%, from 95% to 99%, from 95% to 98%, from 95% to 97%, and from 95% to 96%) of the nilotinib is in amorphous form.

The solid dispersion can be in a single phase such as substitutional or interstitial crystalline solutions or amorphous solutions; or it can be a two-phase system such as eutectics, crystalline drug and amorphous carrier or amorphous drug and amorphous carrier dispersions. Solid solutions are a resultant single phase upon dispersion of two compounds in each other, at their molecular level.

The inventors of the present application have found that a composition comprising amorphous solid dispersion of nilotinib or its pharmaceutically acceptable salts comprising at least one pharmaceutically acceptable carrier and at least one organic acid at a certain ratio, can increase the solubility of nilotinib in gastrointestinal tract, and can ameliorate the problem of precipitation or crystallization, thereby increasing the absorption of nilotinib in vivo and bioavailability thereof.

In another aspect, the composition can alter the absorption behavior of nilotinib in vivo, increasing $C_{max}$ and AUC without prolonging $T_{max}$ in fasted state.

In certain aspects, a pharmaceutically acceptable carrier used in the solid dispersion may be an enteric or a non-enteric polymer.

The enteric polymers are selected from the group consisting of cellulose acetate phthalate, cellulose acetate trimellitate, cellulose acetate succinate, methyl cellulose phthalate, ethylhydroxymethylcellulose phthalate, hydroxypropylmethylcellulose phthalate (HPMCP), hydroxypropylmethyl cellulose acetate succinate (HPMC-AS), hydroxypropylmethyl cellulose acetate maleate, hydroxypropylmethylcellulose trimellitate, carboxymethylethyl cellulose, polyvinyl butyrate phthalate, polyvinyl acetate phthalate, a methacrylic acid/ethyl acrylate copolymer and a methacrylic acid/methyl methacrylate copolymer, preferably selected from the group consisting of HPMCP, HPMC-AS, hydroxypropylmethyl cellulose acetate maleate and hydroxypropylmethylcellulose trimellitate, and more preferably is HPMC-AS.

The non-enteric polymers are selected from the group consisting of hydroxypropyl methylcellulose, hydroxypropyl cellulose, hydroxyethyl cellulose, polyvinylpyrrolidone (povidone), poly(vinylpyrrolidone/vinylacetate) (copovidone), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyvinyl alcohol, partially saponified polyvinylalcohol, macrogolglycerol hydroxystearate, polyethylene glycol, and maltodextrins.

In some aspects, the pharmaceutical composition includes amorphous solid dispersion of the nilotinib or a pharmaceutically acceptable salt thereof, and a pharmaceutically acceptable carrier, where the weight ratio of the nilotinib or a pharmaceutically acceptable salt thereof, to the pharmaceutically acceptable carrier is from about 1:6 to about 1:1 (e.g., from 1:6 to 1:2, from 1:6 to 1:2.5, from 1:6 to 1:3, from 1:6 to 1:3.5, from 1:6 to 1:4, from 1:6 to 1:4.5, from 1:6 to 1:5, from 1:5 to 1:2, from 1:5 to 1:2.5, from 1:5 to 1:3, from 1:5 to 1:3.5, from 1:5 to 1:4, from 1:5 to 1:4.5, from 1:5 to 1:1.5, from 1:4 to 1:1.5, from 1:4 to 1:2, from 1:4 to 1:2.5, from 1:4 to 1:3, from 1:4 to 1:3.5, from 1:3 to 1:1.5, from 1:3 to 1:2, from 1:3 to 1:2.5, and from 1:2 to 1:1.5).

In certain embodiments, nilotinib or its pharmaceutically acceptable salt and pharmaceutically acceptable carrier are present in a ratio of about 1:1 to about 1:6 (w/w), about 1:1 to about 1:4 (w/w), preferably in the ratio of about 1:3 (w/w).

Solid dispersions of the present invention optionally may include one or more organic acids. The organic acid may be selected from acetic acid, propionic acid, octanoic acid, decanoic acid, dodecanoic acid, glycolic acid, lactic acid, fumaric acid, succinic acid, adipic acid, pimelic acid, malic acid, tartaric acid, citric acid, glutamic acid, aspartic acid, maleic acid, benzoic acid, salicylic acid, phthalic acid, phenylacetic acid, cinnamic acid and ascorbic acid. The concentration of organic acid in the inventive compositions may range from about 10 mg to about 300 mg.

In embodiments, nilotinib or its pharmaceutically acceptable salt and organic acid are present in a ratio of 1:0.5 to 1:5, preferably present in a ratio of 1:2, more preferably present in a ratio of 1:1.

Solid dispersions of the present invention optionally may include one or more solubilizers, i.e., additives which increase solubility of the pharmaceutical active ingredient in the solid dispersion or additives which act as pore-forming agents in the solid dispersion. Suitable solubilizers for use in compositions of the present invention include mannitol, transcutol, polyvinylalcohol, hydroxypropyl methylcellulose, hydroxypropyl cellulose, polyvinylpyrrolidone, glycofurol and transcutol. The concentration of solubilizer ranges from about 1% to about 30% w/w of carrier concentration.

The amorphous solid dispersions of the present invention optionally may include one or more surfactants. Surfactants are compounds which are capable of improving the wetting of the drug and/or enhancing the dissolution. The surfactants can be selected from hydrophilic surfactants or lipophilic surfactants or mixtures thereof. The surfactants can be anionic, nonionic, cationic, and zwitterionic surfactants. Surfactants according to the present invention include, but not limited to, polyoxyethylene alkylaryl ethers such as polyoxyethylene lauryl ether, polyoxyethylene cetyl ether, polyoxyethylene stearyl ether; polyethylene glycol fatty acid esters such as PEG monolaurate, PEG dilaurate, PEG distearate, PEG dioleate; polyoxyethylene sorbitan fatty acid ester such as polysorbate 40, polysorbate 60, polysorbate 80; sorbitan fatty acid mono esters such as sorbitan monolaurate, sorbitan monooleate, sorbitan sesquioleate, sorbitan trioleate, sodium lauryl sulfate, sodium dioctyl sulfosuccinate (DOSS), lecithin, stearylic alcohol, cetostearylic alcohol, cholesterol, polyoxyethylene ricin oil, polyoxyethylene fatty acid glycerides, cremophor RH 40, and the like or combinations thereof. The concentration of surfactant ranges from about 1% to about 10% w/w of carrier concentration.

In some aspects herein, the percentage loading of nilotinib fumarate or nilotinib tartrate in solid dispersion is from about 1% to about 90% (w/w) (e.g., from 1% to 19%, from 10% to 19%, from 10% to 20%, from 10% to 30%, from 10% to 40%, from 10% to 50%, from 10% to 60%, from 10% to 70%, from 10% to 80%, from 10% to 90%, from 20% to 30%, from 20% to 40%, from 20% to 50%, from 20% to 60%, from 20% to 70%, from 20% to 80%, from 20% to 90%, from 21% to 30%, from 21% to 34%, from 21% to 40%, from 21% to 50%, from 21% to 60%, from 21% to 70%, from 21% to 80%, from 21% to 90%, from 30% to 40%, from 30% to 50%, from 30% to 60%, from 30% to 70%, from 30% to 80%, from 30% to 90%, from 36% to 40%, from 36% to 49%, from 36% to 60%, from 36% to 70%, from 36% to 80%, from 36% to 90%, from 40% to 50%, from 40% to 60%, from 40% to 70%, from 40% to 80%, from 40% to 90%, from 50% to 60%, from 50% to 70%, from 50% to 80%, from 50% to 90%, 51% to 60%, from 51% to 70%, from 51% to 80%, from 51% to 90%, from 60% to 70%, from 60% to 80%, from 60% to 90%, from 70% to 80%, and from 70% to 90%). In some preferred embodiments, the percentage loading of nilotinib fumarate or nilotinib tartrate is from about 10% to about 60% (w/w) (e.g., from 10% to 20%, from 10% to 30%, from 10% to 40%, from 10% to 50%, from 10% to 60%, from 20% to 30%, from 20% to 40%, from 20% to 50%, from 20% to 60%, from 30% to 40%, from 30% to 50%, from 30% to 60%, from 40% to 50%, and from 40% to 60%).

Solid dispersions of the present application are obtained by one or more of methods selected from spray-drying, solvent evaporation, co-precipitation, hot melt extrusion, co-grinding and lyophilization. The solid dispersions obtained by the present application may be present either in crystalline form or in amorphous form.

In an embodiment, amorphous solid dispersions of nilotinib or its pharmaceutically acceptable salts are obtained by hot melt extrusion. The term hot-melt extrusion or hot-melt extruded is used herein to describe a process whereby a composition is heated and/or compressed to a molten (or softened) state and subsequently forced through an orifice in a die where the extruded product is formed into its final shape in which it solidifies upon cooling. The blend is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. The die can be a dual manifold, multi-manifold or feed-block style die.

The hot-melt extrusion used for the preparation of the pharmaceutical composition of the present invention has to be conducted at temperatures below 200° C. Preferably, the hot-melt extrusion is conducted at a temperature of 30-170° C., more preferred at a temperature of 120-160° C. The hot-melt extrusion has to be carried out at a temperature that allows the dissolution of the nilotinib or its pharmaceutically acceptable salts used as staring material within the mixture of enteric polymer and optionally at least one organic acid.

In an embodiment, amorphous solid dispersions of nilotinib or its pharmaceutically acceptable salts are obtained by spray drying process. Spray dried dispersions are obtained by dissolving drug and the carrier in an organic solvent and then spray-drying the solution. The formulation and process conditions are chosen so that the solvent quickly evaporates from the droplets, allowing insufficient time for phase separation or crystallization.

In an embodiment, nilotinib or its pharmaceutically acceptable salt, at least one enteric polymer and optionally at least one organic acid are mixed with one or more of organic solvents. Suitable solvents for mixing are selected from methanol, ethanol, isopropanol (IPA), ethyl acetate, dichloromethane (DCM), ethylene chloride, chloroform, acetonitrile, acetone and mixtures thereof.

In an embodiment, spray dried amorphous solid dispersions of nilotinib or its pharmaceutically acceptable salts are obtained by a process comprising; mixing nilotinib or its pharmaceutically acceptable salt, at least one enteric polymer and optionally at least one organic acid in a mixture of DCM and methanol (1:1) and spray drying the solution using spray drier. In another embodiment, spray dried amorphous solid dispersions of nilotinib are obtained by a process comprising; mixing nilotinib or its pharmaceutically acceptable salt, at least one enteric polymer and optionally at least one organic acid in methanol and spray drying the solution using spray drier. The spray drying equipment, solvent quantities and process conditions are selected by one skilled in the art based on requirements.

The resultant amorphous solid dispersions of nilotinib fumarate or nilotinib tartrate can be blended with one or more excipients, as described herein, and then granulated and/or compacted to produce a final blend for encapsulating or tableting. In particular embodiments, the amorphous solid dispersion of nilotinib may be combined with one or more excipient(s) may be included to form granules, e.g., such as a binding agent, a filler, a disintegrating agent, a wetting agent, a glidant, and a lubricant.

Pharmaceutical Compositions Comprising Solid Dispersions of Nilotinib

The solid dispersion may be used for filling any one of the unit dosage forms described herein (e.g., a capsule) or for tableting. The solid dispersion can optionally be further processed before filling or tableting. Exemplary further processing includes spheronizing, pelletizing, milling, injection molding, sieving, and/or calendering the solid dispersion.

Amorphous solid dispersions of nilotinib or its pharmaceutically acceptable salts of the present application can be optionally subjected to a particle size reduction procedure before or after the completion of drying of the product to produce desired particle sizes and distributions. Milling or micronization can be performed to achieve the desired particle sizes or distributions. Equipment that may be used for particle size reduction include, without limitation thereto, ball mills, roller mills, hammer mills, and jet mills.

In another general aspect, there is provided solid dispersion of nilotinib comprising amorphous form of nilotinib having particle size distributions wherein D90 is less than about 500 microns or less than about 200 microns or less than about 100 microns or less than about 50 microns or less than about 40 microns or less than about 30 microns or less than about 20 microns or less than about 10 microns or any other suitable particle sizes.

The amorphous solid dispersion of nilotinib fumarate or nilotinib tartrate may be combined with pharmaceutically acceptable excipients to make other pharmaceutical compositions, or a finished dosage form. The one or more additional pharmaceutically acceptable excipients are selected from diluents, binders, disintegrants, lubricants, glidants, surfactants, solubilizers, stabilizing agents, antioxidants, colors, flavors, preservatives, and combinations thereof.

In an embodiment, pharmaceutical compositions comprising amorphous solid dispersion of nilotinib fumarate or nilotinib tartrate and pharmaceutically acceptable excipients are prepared by using, but not limited, to wet granulation, dry granulation, and direct compression.

In an embodiment, pharmaceutical compositions comprising amorphous solid dispersion of nilotinib or pharmaceutically acceptable salts thereof and pharmaceutically acceptable excipients are prepared by using direct compression, which process comprises mixing amorphous solid dispersion of nilotinib and pharmaceutically acceptable excipients, the resultant mixture is either compressed to tablet or filled in hard gelatin capsules.

In an embodiment, pharmaceutical compositions comprising amorphous solid dispersion of nilotinib fumarate or nilotinib tartrate and pharmaceutically acceptable excipients are prepared by using dry granulation, wherein dry granulation is carried out by either direct compaction or roller compaction or both.

In an embodiment, pharmaceutical compositions comprising amorphous solid dispersion of nilotinib fumarate or nilotinib tartrate and pharmaceutically acceptable excipients are prepared by using direct compaction dry granulation, which process comprises compressing mixture of amorphous solid dispersion of nilotinib fumarate or nilotinib tartrate and intragranular material into slug, compressed slugs are milled and passed through mess screen manually or automatically which results in granules. The resulting granules were mixed with extra-granular material. This final mixture is either compressed to tablet or filled in hard gelatin capsules.

In an embodiment, pharmaceutical compositions comprising amorphous solid dispersion of nilotinib fumarate or nilotinib tartrate and pharmaceutically acceptable excipients are prepared by using roller compaction dry granulation, which process comprises passing a mixture of amorphous solid dispersion of nilotinib fumarate or nilotinib tartrate and intragranular material between two high-pressure rollers to form consolidated and densified material, the resultant densified material is then reduced to a uniform granule size by milling, which were then mixed with extra-granular material. This final mixture is either compressed to tablet or filled in hard gelatin capsules.

In an embodiment, pharmaceutical compositions comprising amorphous solid dispersion of nilotinib fumarate or nilotinib tartrate and pharmaceutically acceptable excipients are prepared by wet granulation, which process comprises: (a) mixing amorphous solid dispersion of nilotinib fumarate or nilotinib tartrate and pharmaceutically acceptable excipients (b) adding sufficient solvent, wherein the solvent is selected form water, isopropanol, ethanol, to the mixture obtained from step (a) under shear to generate granules; (c) milling or grinding the granules followed by sieving of said granules; optionally mixing with other excipients. This final mixture is either compressed to tablet or filled in hard gelatin capsules.

The invention also relates to compositions comprising amorphous solid dispersion of nilotinib fumarate or nilotinib tartrate for oral administration, which solid dispersion further comprises at least one pharmaceutically acceptable carrier and optionally at least one organic acid, which composition comprises (a) an immediate-release portion and (b) a modified-release portion, wherein the organic acid may be present either in immediate-release or modified-release portion or may be present in both the portions.

As used herein the term "immediate-release" refers to the rapid release of the majority of the therapeutic compound. Particularly useful conditions for immediate-release are release of at least or equal to about 80% of the therapeutic compound within thirty minutes after oral ingestion. The particular immediate-release conditions for a specific therapeutic compound will be recognized or known by one of ordinary skill in the art.

As used herein the term "modified-release" refers to slower release of the majority of the therapeutic compound as compared to immediate release dosage forms. The particular modified-release conditions for a specific therapeutic compound will be recognized or known by one of ordinary skill in the art.

The compositions are manufactured by processes such as direct compression, wet granulation or dry granulation. The pharmaceutical compositions are in the form of oral dosage forms, preferably solid oral dosage forms, including capsules, tablets and multi-particulates.

Physically, the combination of active ingredient and vehicle may either form a solid dispersion, i.e., the active ingredient is dispersed in the vehicle in particulate form, or may form a solid solution, i.e., the active ingredient is dissolved in the vehicle at a molecular level. The active ingredient and the vehicle may also form a solid dispersion having therein a part of the active ingredient dissolved at a molecular level. The physical state of the dispersion and/or solution may be determined by using various techniques such as Hot Stage Microscopy (HSM), Differential Scanning Calorimetry (DSC), Scanning Electron Microscopy (SEM) optionally in combination with Energy Dispersive X-ray (EDX), and X-ray powder diffraction.

In an embodiment, inventive amorphous solid dispersions of nilotinib tartrate of the present application comprise nilotinib tartrate, at least one enteric polymer and at least one organic acid, wherein the enteric polymer is HPMC-AS and the organic acid is tartaric acid. Specifically, nilotinib tartrate and HPMC-AS are present in a ratio of 1:3 (w/w), nilotinib tartrate and tartaric acid are present in a ratio of 1:1 (w/w).

In an embodiment, inventive amorphous solid dispersions of nilotinib fumarate of the present application comprise nilotinib fumarate, at least one enteric polymer and at least one organic acid, wherein the enteric polymer is HPMC-AS and the organic acid is fumaric acid. Specifically, nilotinib fumarate and HPMC-AS are present in a ratio of 1:3 (w/w), nilotinib fumarate and fumaric acid are present in a ratio of 1:1 (w/w).

An embodiment relates to pharmaceutical compositions comprising amorphous solid dispersions of nilotinib fumarate or nilotinib tartrate for oral administration, wherein at least 30% of nilotinib fumarate or nilotinib tartrate is released within 60 minutes as determined by USP dissolution apparatus II (paddle) at 75 rotations per minute (rpm) in 500 mL of 0.01M HCl as dissolution medium.

Another embodiment relates to pharmaceutical compositions comprising amorphous solid dispersions of nilotinib fumarate or nilotinib tartrate for oral administration, wherein at least 30% of nilotinib fumarate or nilotinib tartrate is released within 60 minutes in 0.01M HCl media, as determined using USP dissolution apparatus II (paddle) at 75 rpm in 500 mL of 0.01M HCl media for 60 minutes followed by 900 mL of pH 5.0±0.05 FeSSIF media buffer and FaSSIF media buffer for 90 minutes at 37±0.5° C.

In an embodiment, the obtained amorphous solid dispersions of nilotinib fumarate or nilotinib tartrate are combined with other pharmaceutically acceptable excipients such as diluents, binders, disintegrating agents, glidants, lubricants, plasticizers, colorants and surfactants to make it into finished dosage form. The pharmaceutical compositions comprising inventive amorphous solid dispersions of nilotinib fumarate or nilotinib tartrate and pharmaceutically acceptable excipients are prepared by using process such as wet granulation, dry granulation, direct compression, preferably dry granulation. The dry granulation process may be carried out either by direct compaction or roller compaction or both.

The pharmaceutical compositions comprising amorphous solid dispersions of nilotinib or its pharmaceutically acceptable salts thereof and pharmaceutically acceptable excipients can be prepared by using direct compaction dry granulation, which process comprises of compressing mixture of the amorphous solid dispersions of nilotinib and intra-granular excipients into slug; compressed slugs are milled and passed through mess screen manually or automatically. The resulting granules are mixed with extra-granular excipients. This final mixture is either compressed into tablet or filled in capsules.

The pharmaceutical compositions comprising amorphous solid dispersions of nilotinib fumarate or nilotinib tartrate and pharmaceutically acceptable excipients may also be prepared by using roller compaction dry granulation, which process comprises of passing mixture of solid dispersion and intra-granular excipients between two high-pressure rollers to form consolidated and densified material; the resultant densified material is then reduced to a uniform granule size by milling, which are then mixed with extra-granular excipients. This final mixture is either compressed into tablet or filled in capsules.

The pharmaceutical compositions comprising amorphous solid dispersions of nilotinib fumarate or nilotinib tartrate and pharmaceutically acceptable excipients may also be prepared by using direct compression, which process comprises of mixing the amorphous solid dispersions of nilotinib fumarate or nilotinib tartrate and pharmaceutically acceptable excipients; the resultant mixture is either compressed into tablets or filled in capsules.

The pharmaceutical compositions comprising amorphous solid dispersions of nilotinib fumarate or nilotinib tartrate and pharmaceutically acceptable excipients can also be prepared by wet granulation, which process comprises of: (a) mixing amorphous solid dispersions of nilotinib fumarate or nilotinib tartrate and pharmaceutically acceptable excipients (b) adding sufficient solvent, wherein the solvent is selected form water, isopropanol, ethanol, to the mixture obtained from step (a) under shear to generate granules; (c) milling or grinding the granules followed by sieving of said granules; optionally mixing with other excipients. This final mixture is either compressed into tablet or filled in capsules.

The pharmaceutical composition of the present invention is preferably a granulate/particulate material. The granules/particles may be filled into a capsule or compressed into a tablet. The tablet may optionally be coated with an additional enteric polymer or an immediate-release coating.

Moreover, the extrudates/granules of the present invention may be formulated into any suitable dosage form, including but not limited to oral suspensions, gels, tablets, capsules, immediate release formulations, delayed release formulations, controlled release formulations, extended release formulations, pulsatile release formulations, and mixed immediate and controlled release formulations.

Other pharmaceutically acceptable excipients may include, but are not limited to, diluents, binders, disintegrating agents, surfactants, plasticizers, lubricants, glidants, chelating agents, coating agents and the like or mixtures thereof as extra-granular agents.

Suitable diluents include microcrystalline cellulose, calcium carbonate, calcium phosphate-dibasic, calcium phosphate-tribasic, calcium sulfate, cellulose powdered, dextrates, dextrins, dextrose excipients, fructose, kaolin, lactitol, lactose, mannitol, sorbitol, starch, starch pregelatinized, sucrose, sugar compressible, sugar confectioners and the like.

In an embodiment, diluent is included either in intra-granular portion or extra-granular portion or both. The diluent concentration ranges from about 10% to about 60% w/w of total composition. The diluent concentration in the intra-granular portion ranges from about 10% to about 60% w/w of total composition, preferably about 25% to about 35%.

Suitable binders include methyl cellulose, hydroxypropyl cellulose, hydroxypropyl methylcellulose, polyvinyl pyrrolidone, microcrystalline cellulose, gelatin, gum arabic, ethyl cellulose, polyvinyl alcohol, pullulan, pregelatinized starch, agar, tragacanth, sodium alginate, propylene glycol and the like. The concentration of binder ranges from about 1% to about 20% w/w of total composition, preferably about 10% to about 15% w/w.

Suitable disintegrating agents include croscarmellose sodium, low-substituted hydroxypropyl cellulose (L-HPC), sodium starch glycollate, carboxymethyl cellulose, calcium carboxymethyl cellulose, sodium carboxymethyl cellulose, starch, crystalline cellulose, hydroxypropyl starch, pregelatinized starch, and the like and mixtures thereof. The concentration of disintegrating agent ranges from about 1% to about 10% w/w of total composition.

Suitable lubricants/glidants include colloidal silicon dioxide (AEROSIL®), stearic acid, magnesium stearate, calcium stearate, talc, hydrogenated castor oil, sucrose esters of fatty acid, microcrystalline wax, yellow beeswax, white beeswax, and the like and mixtures thereof. The concentration of lubricant/glidant ranges from about 0.5% to about 5% w/w of total composition.

Suitable surfactants include both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as "poloxamer;" ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof. The concentration of surfactant ranges from about 0.5% to about 10% w/w of total composition.

Suitable plasticizers include polyethylene glycol, propylene glycol, polyethylene oxide, 1,2-butylene glycol, 2,3-butylene glycol, styrene glycol, diethylene glycol, triethylene glycol, tetraethylene glycol and monoisopropyl ether, propylene glycol monoethyl ether, ethylene glycol monoethyl ether, diethylene glycol monoethyl ether, sorbitol lactate, ethyl lactate, butyl lactate, ethyl glycolate, triethyl citrate, acetyl triethyl citrate, tributyl citrate and allyl glycolate. The concentration of plasticizer ranges from about 0.5% to about 10% w/w of total composition.

Suitable colouring agent include dyes and pigments such as iron oxide red or yellow, titanium dioxide, talc. The concentration of colouring agent ranges from about 0.1% to about 1% w/w of total composition.

Suitable chelating agents include, one or more of, but not limited to ethylenediaminetetraacetic acid (EDTA), disodium EDTA and derivatives thereof, citric acid and derivatives thereof, niacinamide and derivatives thereof, and sodium desoxycholate and the like or mixtures thereof. The concentration of chelating agent ranges from about 0.1% to about 1% w/w of total composition.

The pharmaceutical composition, may also optionally be coated, i.e., seal coated and/or enteric coated and/or film coated. Preferably, the pharmaceutical composition may be seal coated and finally film coated or it may be seal coated and further enteric coated. Optionally, pharmaceutical compositions of the invention may be film coated. Preferably, the film coating polymer may be present in an amount from about 2 to 10% w/w.

In an embodiment, the invention relates to pharmaceutical compositions comprising amorphous solid dispersions of nilotinib fumarate or nilotinib tartrate for oral administration, which solid dispersion comprises at least one pharmaceutically acceptable carrier and optionally at least one organic acid, having a fed/fasted ratio of 0.8-1.5 for AUC and/or $C_{max}$.

Another embodiment relates to pharmaceutical compositions comprising amorphous solid dispersions of nilotinib fumarate or nilotinib tartrate for oral administration, which solid dispersion comprises at least one pharmaceutically acceptable carrier and optionally at least one organic acid, having a fasted state bioavailability that exceeds 130% of the commercially available product.

In yet another embodiment, the invention relates to a kit comprising a) a solid dosage form comprising an effective amount of amorphous solid dispersions of nilotinib fumarate or nilotinib tartrate and a pharmaceutically acceptable carrier, and b) instructions for oral administration of the dosage form (a), which i) do not specify administration with food, or ii) indicate that the dosage form (a) may be administered without regard to food.

Certain embodiments relate to pharmaceuticals compositions as described herein, which are stable, e.g., stable over the shelf life of the drug product. As used herein, the term "stable" is defined as no more than about 5% loss of nilotinib under typical commercial storage conditions. In certain embodiments, the formulations of the present invention will have no more than about 3% loss of nilotinib, more preferably, no more than about 2% loss of nilotinib, under typical commercial storage conditions. The composition retains at least about 95% of the potency of nilotinib after storing the composition at 40° C. and 75% relative humidity for at least three months. In certain aspects, the term "stable" refers to chemical stability, wherein not more than 1.5% w/w of total related substances are formed on storage at accelerated conditions of stability at 40° C. and 75% relative humidity or at 25° C. and 60% relative humidity for a period of at least three months or to the extent necessary for use of the composition.

Dosage and Administration

The dose of the therapeutic compound will be in the range from about 0.1 to about 1000 mg per kilogram body weight of the recipient per day. Exemplary unit doses of therapeutic compound range from 20 mg to 1000 mg, including unit dosages of 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg, 550 mg, 600 mg and 800 mg. Alternatively lower doses may be given, for example doses of 0.5 to 100 mg; 0.5 to 50 mg; or 0.5 to 20 mg per kilogram body weight per day. The effective dosage range of the pharmaceutically acceptable salts may be calculated based on the weight of the active moiety to be delivered. If the salt exhibits activity itself, the effective dosage may be estimated as above using the weight of the salt, or by other means known to those skilled in the art.

Methods of Treatment

The invention provides methods of therapeutically treating proliferative disorders by administering a quantity of: a composition of the invention; formulation comprising a composition of the invention; or dosage form comprising a composition of the invention, which administered quantity provides from about 25 mg to about 500 mg of nilotinib per day, either in a single or divided dose. In some embodiments it is preferred to administer daily, in either a single or divided dose an amount of: a composition of the invention or dosage form comprising a composition of the invention which provides from about 50 mg to about 400 mg of nilotinib, preferably at least about 50 mg, 150 mg and 200 mg of nilotinib. In some embodiments it is preferred to provide treatment by administering from about 300 mg of nilotinib to about 400 mg of nilotinib per day.

The pharmaceutical composition according to the present invention improves the absorption behavior of nilotinib in human body, and increases the absorption and bioavailability of the drug in comparison to the commercially available nilotinib formulation (TASIGNA®).

In certain embodiments, the dose of nilotinib is at the most about 98% w/w, or at the most about 95% w/w, or at the most about 90% w/w, or at the most about 85% w/w, or at the most about 80% w/w, or at the most about 75% w/w, or at the most about 70% w/w, or at the most about 65% w/w, or at the most about 60% w/w, or at the most about 55% w/w or at the most about 50% w/w of the dose of the nilotinib administered in the form of a commercially available product.

In an embodiment, the invention relates to a method for treating a proliferative disorder in a human, which method comprises administering a) a solid dosage form comprising an effective amount of amorphous solid dispersions of nilotinib fumarate or nilotinib tartrate and a pharmaceutically acceptable carrier; and b) instructions for oral administration of the dosage form (a), which i) do not specify administration with food, or ii) indicate that the dosage form (a) may be administered without regard to food.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

For administration to animal or human subjects, the pharmaceutical compositions comprise an effective dosage amount of nilotinib or a pharmaceutically acceptable salt thereof. The formulation may be prepared using conventional methods, for example, depending on the subject to be treated, the mode of administration, and the type of treatment desired (e.g., prevention, prophylaxis, or therapy).

The nilotinib or pharmaceutically acceptable salt thereof, may be present in amounts totaling 1-95% by weight of the total weight of the composition.

Preferably, the pharmaceutical composition will be provided in a dosage form that is suitable for oral administration, including but not limited to hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, lozenges, films, strips, suspensions, syrups, or sprinkles. The compositions may be formulated according to conventional pharmaceutical practice.

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

In an aspect, the invention relates to certain methods of treatment comprising administration of a pharmaceutical composition described herein, where the total daily dosage amount is 400 mg, 600 mg or 800 mg.

Preferred unit dosage amounts include 15 mg, 20 mg, 25 mg, 30 mg, 35 mg, 40 mg, 45 mg, 50 mg, 75 mg, 100 mg, 125 mg, 150 mg, 175 mg, or 200 mg of nilotinib or a pharmaceutically acceptable salt thereof.

The term "unit dosage form" refers to a physically discrete unit suitable as a unitary dosage, such as a tablet, caplet, hard capsule, or soft capsule, each unit containing a predetermined quantity of a drug.

By "effective" amount is meant the amount of a drug sufficient to treat, prevent, or ameliorate a condition in a subject or patient. The effective amount of nilotinib or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

Dissolution Testing

In an embodiment, amorphous solid dispersions of nilotinib fumarate or nilotinib tartrate and pharmaceutical compositions manufactured in the present application were tested for comparative dissolution by using USP apparatus-II (paddle) in 0.01M HCl followed by buffer (FaSSIF and/or FeSSIF) media. Preparation of dissolution media required for the studies was prepared as described below.

Preparation of 0.01M HCl (3.5 L):
2.9 mL of 37% HCl was added into 3.5 L purified water
Preparation of Double Strength FaSSIF (3 L):
To 3 liters of purified water was added: 2.53 g sodium hydroxide, 23.7 g sodium dihydrogen phosphate monohydrate, and 37.1 g sodium chloride, followed by mixing thoroughly. Once mixed, the pH was adjusted to 6.50±0.05 with sodium hydroxide or hydrochloric acid. Once the pH was adjusted, 13.6 g FaSSIF powder was added and mixed thoroughly.

Preparation of Double Strength FeSSIF (2.5 L)
To 2.5 liters of purified water was added: 20.2 g sodium hydroxide, 43.3 g glacial acetic acid, and 59.4 g sodium chloride, followed by mixing thoroughly. Once mixed, the pH was adjusted to 5.0±0.05 with sodium hydroxide or acetic acid. Once the pH was adjusted, 56.0 g FaSSIF powder was added and mixed thoroughly.

The samples withdrawn from the dissolution study were analyzed for drug content using the following HPLC procedure. The materials and general conditions are listed below:

TABLE 1

| Chromatographic conditions | |
|---|---|
| Chromatographic Mode | Isocratic 35:65 (Mobile phase A):(Mobile phase B) |
| Column | YMC Pack Pro C18, 150 mm × 4.6 mm, 3 μm |
| Wavelength | 230 nm |
| Flow rate | 1.2 mL/min |
| Injection volume | 5 μL |
| Column temperature | 45° C. |
| Run time | 6 minutes |
| Mobile Phase A | 1.36 g of Potassium dihydrogen phosphate and 1 g of 1-octane sulphonic acid sodium salt to 1 liter of water and stir to dissolve. |
| Mobile Phase B | To 850 mL of Acetonitrile, add 100 mL of Methanol and 50 mL of water and mix thoroughly. |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Solid dispersions of nilotinib base having compositions set forth in Table 2 were prepared by spray drying.

TABLE 2

| | Composition | | | | |
|---|---|---|---|---|---|
| Ingredients | 1 % w/w | 2 % w/w | 3 % w/w | 4 % w/w | 5 % w/w |
| Nilotinib base | 33.3 | 25 | 20 | 33.3 | 25 |
| HPMC-AS | 66.6 | 75 | 80 | — | — |
| HPMCP 55 | — | — | — | 66.6 | 75 |
| DCM:Methanol (3:1) | q.s. | q.s. | q.s. | q.s. | q.s. | q.s.: quantity sufficient

Manufacturing Procedure:
The required quantities of nilotinib base and the selected carrier (i.e., HPMC-AS and HPMCP 55) according to Table 2, were dissolved in a mixture of dichloromethane (DCM) and methanol in 3:1 ratio, to provide a feeder solution. The obtained feeder solution was passed through a nozzle as a fine spray into a chamber where the solvent was evaporated quickly to generate particles containing the nilotinib and carrier. The resulting spray dried powder was dried further to remove residual solvents in a static dryer. Powder X-ray diffraction patterns of nilotinib base solid dispersion of composition 2 and 5 were provided in FIG. 1. The total weight of each composition was 100 grams.

Example 2

Solid dispersions of nilotinib fumarate having the compositions set forth in Table 3 were prepared by spray drying.

TABLE 3

| | Composition | | | | | | |
|---|---|---|---|---|---|---|---|
| Ingredients | 6 % w/w | 7 % w/w | 8 % w/w | 9 % w/w | 10 % w/w | 11 % w/w | 12 % w/w |
| Nilotinib fumarate | 33.3 | 25 | 20 | 33.3 | 25 | 33.3 | 25 |
| HPMC-AS | 66.6 | 75 | 80 | — | — | — | — |
| PVP K30 | — | — | — | 66.6 | 75 | — | — |
| HPMC E3 | — | — | — | — | — | 66.6 | 75 |
| Methanol | q.s. | q.s. | q.s. | q.s. | q.s. | q.s. | q.s. |
| Dichloromethane | — | — | — | q.s. | q.s. | q.s. | q.s. | q.s.: quantity sufficient

Manufacturing Procedure:

The required quantities of nilotinib fumarate and carrier (i.e., HPMC-AS, PVP K30 or HPMC E3), according to Table 3 were dissolved in methanol and/or dichloromethane, to provide feeder solutions. The obtained feeder solutions were passed through nozzles as fine spray into chambers where the solvents (i.e., methanol and dichloromethane) were evaporated quickly to generate powders. The resulting spray dried powders were further dried to remove residual solvents in a static dryer. The total weight of each prepared composition was 100 grams.

Example 3

Solid dispersions of nilotinib fumarate having the compositions set forth in Table 4 were prepared by spray drying.

TABLE 4

| | Composition | | | | | |
|---|---|---|---|---|---|---|
| | 13 | | 14 | | 15 | |
| Ingredients | Qty(g) | % w/w | Qty(g) | % w/w | Qty(g) | % w/w |
| Nilotinib fumarate | 4.13 | 20.6 | 4.13 | 20.6 | 4.13 | 20.6 |
| HPMC-AS | 12.45 | 62.3 | — | — | — | — |
| PVP K30 | — | — | 12.45 | 62.3 | — | — |
| HPMC E3 | — | — | — | — | 12.45 | 62.3 |
| Fumaric acid | 3.41 | 17.1 | 3.41 | 17.1 | 3.41 | 17.1 |
| Methanol | q.s. | q.s. | q.s. | q.s. | q.s. | q.s. |
| Dichloromethane | — | — | q.s. | q.s. | q.s. | q.s. | q.s.: quantity sufficient

Manufacturing Procedure:

The required quantities of nilotinib fumarate, HPMC-AS, PVP K30, HPMC E3 and fumaric acid as mentioned in Table 4 were dissolved in methanol, to provide feeder solutions. The obtained feeder solutions were passed through nozzles as fine spray into chambers where solvents (i.e., methanol and dichloromethane) were evaporated quickly to generate powders. The obtained spray dried powders were dried further to remove residual solvents in astatic dryer. Total weight of each composition is 20 grams.

Figure 2:
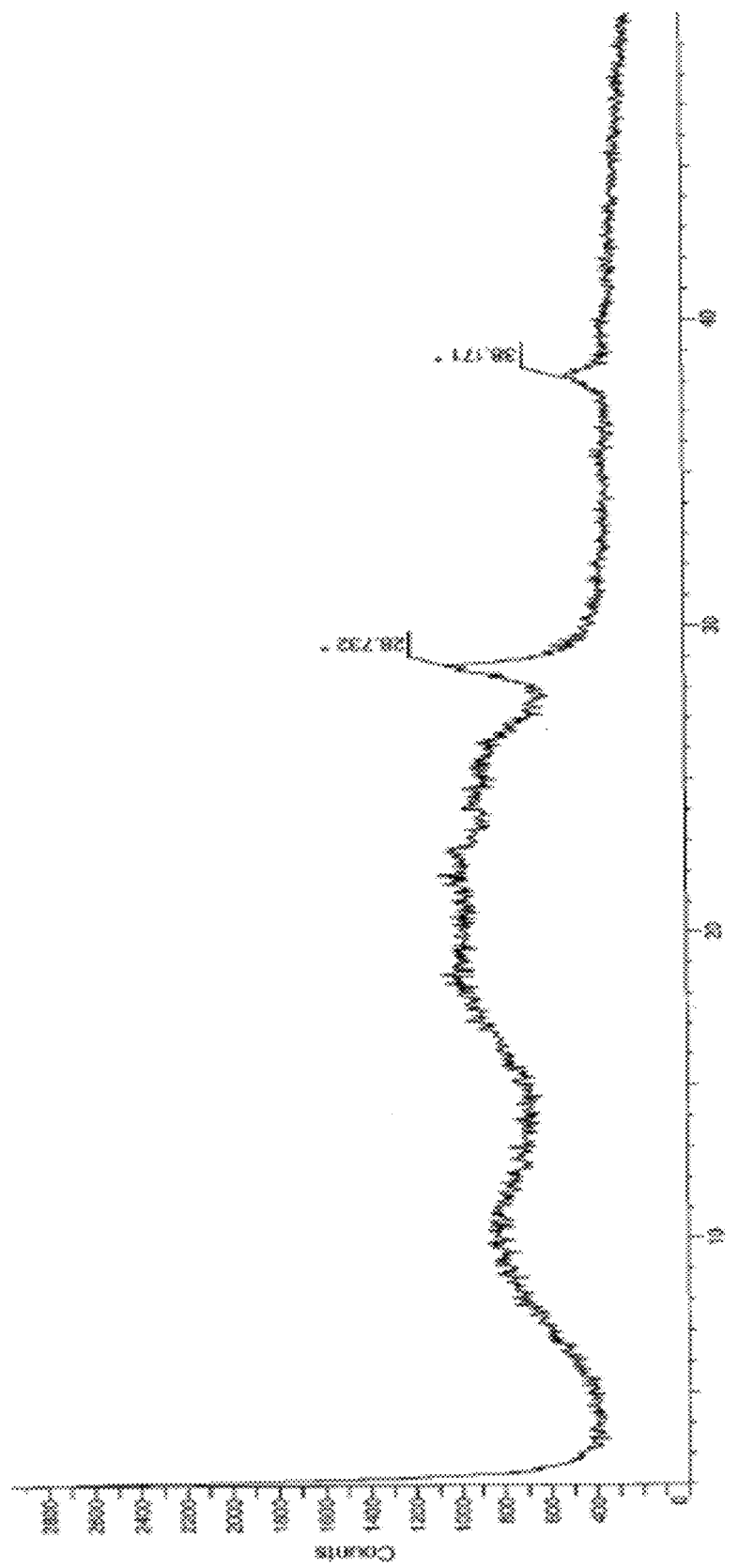
FIG. 2 illustrates the powder X-ray diffraction pattern of the amorphous solid dispersion of nilotinib fumarate according to Composition 13 from Example 3.

The powder X-ray diffraction pattern (PXRD) for the amorphous solid dispersion of nilotinib fumarate of Composition 13 is illustrated in FIG. 2.

Example 4

Solid dispersions of nilotinib tartrate having composition set forth in Table 5 were prepared by spray drying.

TABLE 5

| | Composition | | | |
|---|---|---|---|---|
| | 16 | | 17 | |
| Ingredients | Qty(g) | % w/w | Qty(g) | % w/w |
| Nilotinib tartrate | 25 | 25 | 20.4 | 20.4 |
| HPMC-AS | 75 | 75 | 63.7 | 63.7 |
| Tartaric acid | — | — | 15.9 | 15.9 |
| Methanol | q.s. | q.s. | q.s. | q.s. |

Manufacturing Procedure:

The required quantities of nilotinib tartrate, HPMC-AS and tartaric acid as mentioned in Table 5 were dissolved in methanol to prepare feeder solutions. The obtained feeder solutions were passed through nozzles as fine spray into chambers where methanol was evaporated quickly to generate powders. The resulting spray dried powders were dried further to remove residual solvent in a static dryer. Total weight of each prepared composition was 100 grams.

Figure 3:
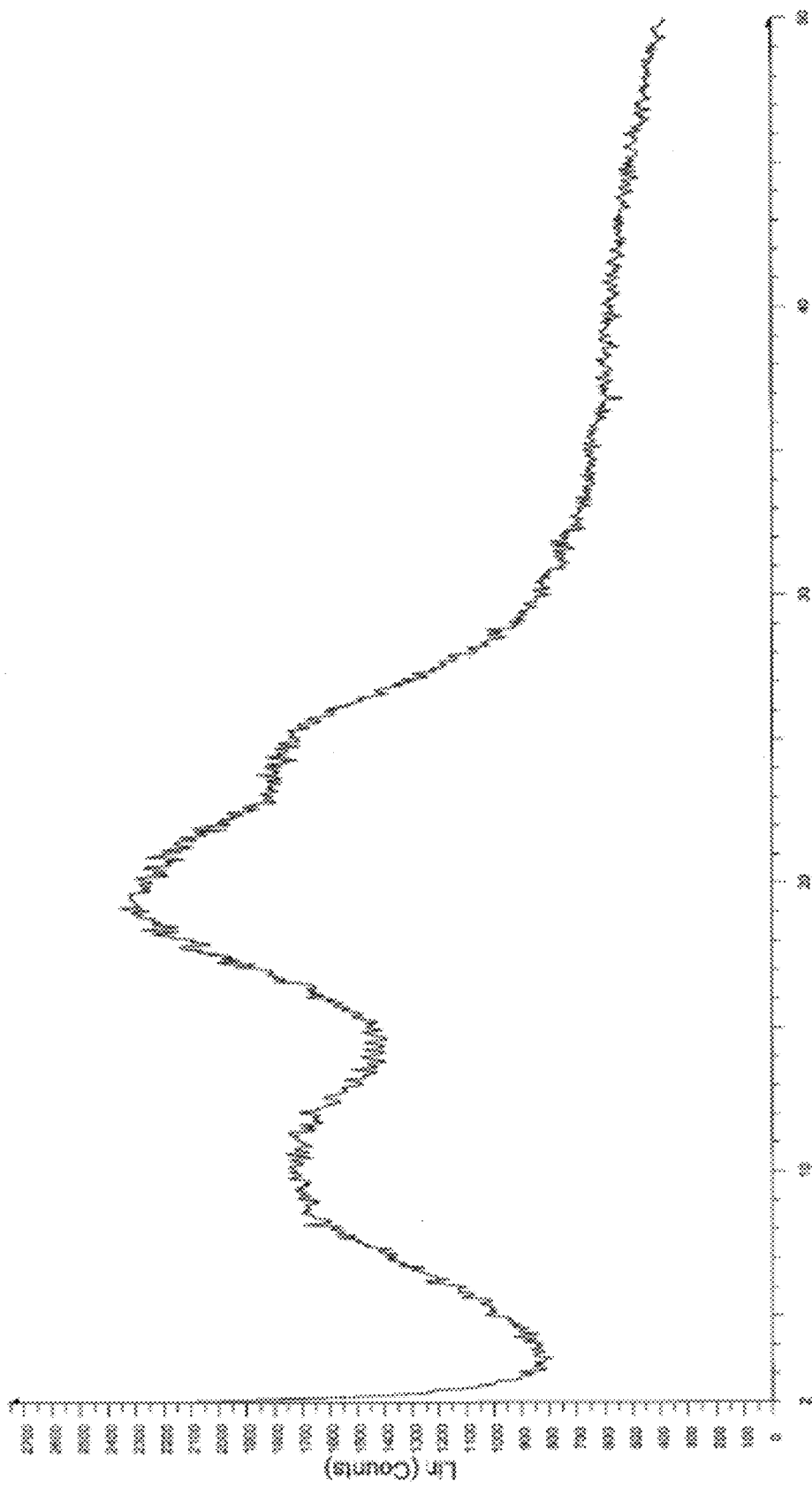
FIG. 3 illustrates powder X-ray diffraction pattern of Composition 16 from Example 4.

Powder X-ray diffraction pattern of Composition 16 is illustrated in FIG. 3. Instrument used for spray drying in the above examples 1-4 was Buchi B-290 mini-spray dryer and parameters of spray drying were given below:

Total dissolved solids: 10% w/v

Inlet Temperature (° C.): 120

Aspirator rate: 100%

Nozzle type: twin fluid nozzle

Nozzle pressure: 50 psi

Feed rate: 10 mL min$^{-1}$

Example 5

Solid dispersions of nilotinib tartrate having the compositions set forth in Table 6 were prepared by hot-melt extrusion (HME).

TABLE 6

| | Composition | | | | | | |
|---|---|---|---|---|---|---|---|
| Ingredients | 18 % w/w | 19 % w/w | 20 % w/w | 21 % w/w | 22 % w/w | 23 % w/w | 24 % w/w |
| Nilotinib tartrate | 33.3 | 25 | 20 | 33.3 | 25 | 33.3 | 25 |
| HPMC-AS | 66.6 | 75 | 80 | — | — | — | — |
| HPMC E3 | — | — | — | 66.6 | 75 | — | — |
| PVP K30 | — | — | — | — | — | 66.6 | 75 |

Manufacturing Procedure:

The required quantities of nilotinib tartrate, HPMC-AS, HPMC E3 and PVP K30 were weighed as mentioned in the Table 6 and physically mixed in a polybag. The resultant mixtures were then placed in an extruder hopper separately. The mixtures were passed through the heated extruder at a temperature range from about 30° C. to about 170° C., as determined by temperature setting of the extruder heating zones so that melting or softening of the carrier occurred. The resulting extrudate was cooled to room temperature and milled, then the milled material was sifted through a 30-mesh screen. Total weight of each prepared composition was 100 grams.

Example 6

Solid dispersions of nilotinib tartrate having compositions set forth in Table 7 were prepared by hot melt extrusion (HME).

TABLE 7

| Ingredients | Composition |  |  |  |  |  |  |  |  |
|---|---|---|---|---|---|---|---|---|---|
| | 25 | 26 | 27 | 28 | 29 | 30 | 31 | 32 | 33 |
| | % w/w | | | | | | | | |
| Nilotinib tartrate | 26.4 | 20.4 | 17.3 | 20.5 | 17.0 | 20.5 | 17.0 | 20.5 | 17.0 |
| HPMC-AS | 52.9 | 63.7 | 69.2 | 61.5 | 68.0 | 61.5 | 68.0 | 61.5 | 68.0 |
| Tartaric acid | 20.7 | 15.9 | 13.5 | 16.0 | 13.3 | 16.0 | 13.3 | 16.0 | 13.3 |
| Triethyl citrate (TEC) | — | — | — | 2.05 | 1.69 | — | — | — | — |
| Polyethylene glycol (PEG) | — | — | — | — | — | 2.05 | 1.69 | — | — |
| Propylene glycol | — | — | — | — | — | — | — | 2.05 | 1.69 |

Manufacturing Procedure:

The required quantities of nilotinib tartrate, HPMC-AS, triethyl citrate (TEC), polyethylene glycol (PEG), propylene glycol (PG) and tartaric acid were weighed as mentioned in the Table 7 and physically mixed in a polybag. The resultant mixtures were then placed in an extruder hopper separately, and were passed through heated extruder at a temperature range from about 30° C. to about 170° C., as determined by temperature setting of the extruder heating zones so that melting or softening of the carrier occurred. The resulting extrudate was cooled to room temperature and milled, then the milled material was sifted through a 30-mesh screen. Total weight of each prepared composition was 100 grams.

The Thermofischer11 extruder used in the examples 5 and 6 has a single screw solid conveying mechanism that extends from the hopper through multiple heating zones to the extrusion die. Temperature controls, extruder screw speed, feed rate and the process parameters used during hot-melt extrusion are provided in

TABLE 8

| Zone | Temperature |
|---|---|
| Zone 1 | 33-35° C. |
| Zone 2 | 60° C. |
| Zone 3 | 120° C. |

TABLE 8-continued

| Zone | Temperature |
|---|---|
| Zone 4 | 130° C. |
| Zone 5 | 140° C. |
| Zone 6 | 150° C. |
| Zone 7 | 160° C. |
| Zone 8 | 170° C. |
| Parameters | |
| Die | 2 mm |
| Screw speed | 100 rpm |
| Feed rate | 1 g/minute |

Example 7

Nilotinib capsules were prepared, having the compositions set forth in Table 9.

TABLE 9

| Ingredients | Composition 34 | | Composition 35 | |
|---|---|---|---|---|
| | mg/unit | % w/w | mg/unit | % w/w |
| Nilotinib base (solid dispersion from composition 2) | 200 | 68 | — | — |
| Nilotinib base (solid dispersion from composition 5) | — | — | 200 | 68 |
| Intra-granular material | | | | |
| Microcrystalline cellulose | 73.4 | 25.0 | 73.4 | 25.0 |
| Croscarmellose Sodium | 14.6 | 5.0 | 14.6 | 5.0 |
| AEROSIL ® | 1.5 | 0.5 | 1.5 | 0.5 |
| Magnesium stearate | 1.5 | 0.5 | 1.5 | 0.5 |
| Extra-granular material | | | | |
| AEROSIL ® | 1.5 | 0.5 | 1.5 | 0.5 |
| Magnesium stearate | 1.5 | 0.5 | 1.5 | 0.5 |
| Total | 294 | 100.1 | 294 | 100.1 |

Manufacturing Procedure

1. The required quantities of nilotinib base solid dispersion (from composition 2 or 5) were mixed with intragranular ingredients (i.e., microcrystalline cellulose, croscarmellose sodium, AEROSIL® and magnesium stearate) as mentioned in Table 9.
2. Mixtures obtained were compacted with roller compactor separately. These compacts were milled and passed through a 30-mesh screen to obtain granules, which were blended with AEROSIL® to obtain pre-lubricated blends.

3. Pre-lubricated blends were lubricated with magnesium stearate.
4. Final blends were filled into capsules with respective fill weights for respective strengths of 25 mg to 100 mg.

Dissolution profiles of Composition 34 and 35 in 0.01M HCl Acid Media and Followed by FeSSIF Media of pH 5.0±0.05.

Figure 4:
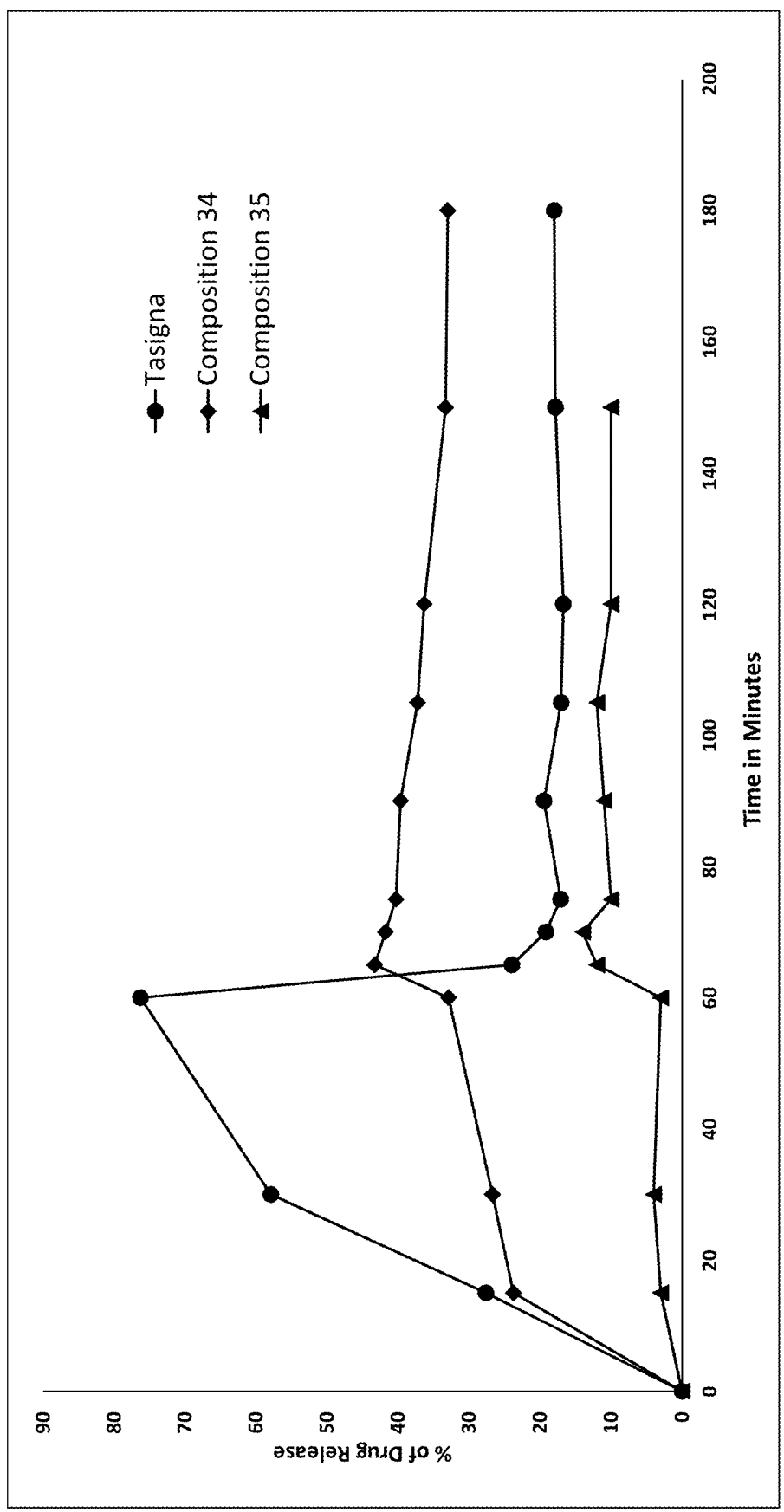
FIG. 4 illustrates comparative dissolution profiles of TASIGNA® 50 mg capsule and Composition 34 and 35 in 0.01 M HCl acid media followed by FeSSIF media of pH 5.0±0.05.

When tested by using USP apparatus II (paddle); 500 mL of 0.01 M HCl media for 60 minutes and followed by 900 mL of pH 5.0±0.05 FeSSIF media for 90 minutes at 37±0.5° C. and stirred at 75 rpm, the dissolution profile of Composition 34 and 35 were compared with TASIGNA® 50 mg capsule in following Table 10. Samples of 5 mL were withdrawn at 15, 30 and 60 minutes in 0.01 M HCl acid media and 65, 70, 75, 90, 105, 120, 150 and 180-minute time points in FeSSIF media. Withdrawn samples were filtered with 0.45 μm nylon membrane filter and then diluted with dimethyl sulfoxide (DMSO) in 1:1 ratio and analysed using HPLC system with UV spectrophotometer at a wavelength 230 nm. The results of the measurements are given in Table 10 and shown graphically in FIG. 4.

TABLE 10

| Dissolution Media | Time (minutes) | TASIGNA® 50 mg Capsule | Composition 34 | Composition 35 |
|---|---|---|---|---|
| 0.01M HCl acid media | 0 | 0 | 0 | 0 |
| | 15 | 28 | 24 | 3 |
| | 30 | 58 | 27 | 4 |
| | 60 | 76 | 33 | 3 |
| FeSSIF media | 65 | 24 | 43 | 12 |
| | 70 | 19 | 42 | 14 |
| | 75 | 17 | 40 | 10 |
| | 90 | 19 | 40 | 11 |
| | 105 | 17 | 37 | 12 |
| | 120 | 17 | 36 | 10 |
| | 150 | 18 | 33 | 10 |
| | 180 | 18 | 33 | — |

Example 8

Nilotinib fumarate capsules were prepared, having the compositions set forth in Table 11.

TABLE 11

| Ingredients | Composition 36 | 37 | 38 | 39 | 40 | 41 | 42 |
|---|---|---|---|---|---|---|---|
| | | | | mg/unit | | | |
| Nilotinib fumarate (solid dispersion from composition 13) | 293 | 263.8 | 205.2 | 146.5 | 263.8 | 205.2 | 146.5 |
| Nilotinib fumarate (solid dispersion from composition 14) | — | 29.3 | 87.9 | 146.5 | — | — | — |
| nilotinib fumarate (solid dispersion from composition 15) | — | — | — | — | 29.3 | 87.9 | 146.5 |
| Intra-granular material | | | | | | | |
| Microcrystalline cellulose | 107.5 | 107.5 | 107.5 | 107.5 | 107.5 | 107.5 | 107.5 |
| Croscarmellose Sodium | 21.4 | 21.4 | 21.4 | 21.4 | 21.4 | 21.4 | 21.4 |
| AEROSIL® | 2.15 | 2.15 | 2.15 | 2.15 | 2.15 | 2.15 | 2.15 |
| Magnesium stearate | 2.15 | 2.15 | 2.15 | 2.15 | 2.15 | 2.15 | 2.15 |
| Extra-granular material | | | | | | | |
| AEROSIL® | 2.15 | 2.15 | 2.15 | 2.15 | 2.15 | 2.15 | 2.15 |
| Magnesium stearate | 2.15 | 2.15 | 2.15 | 2.15 | 2.15 | 2.15 | 2.15 |
| Total | 430.7 | 430.7 | 430.7 | 430.7 | 430.7 | 430.7 | 430.7 |

Manufacturing Procedure:
1. The required quantities of nilotinib fumarate solid dispersion of Composition 13, 14 and 15 were weighed and mixed with intragranular ingredients (i.e., microcrystalline cellulose, croscarmellose sodium, AEROSIL® and magnesium stearate) as mentioned in Table 11.
2. Mixtures obtained were compacted with roller compactor separately, these compacts were milled and passed through a 30-mesh screen separately to obtain granules, which were blended with AEROSIL® to obtain pre-lubricated blends.
3. Pre-lubricated blends were lubricated with magnesium stearate.
4. Final blends were filled into capsules with respective fill weights for respective strengths of 25 mg to 100 mg.

Dissolution Profile of Composition 36 and TASIGNA® 50 mg Capsule in 0.01 M HCl Media Followed by FaSSIF or FeSSIF Media.

Figure 5:
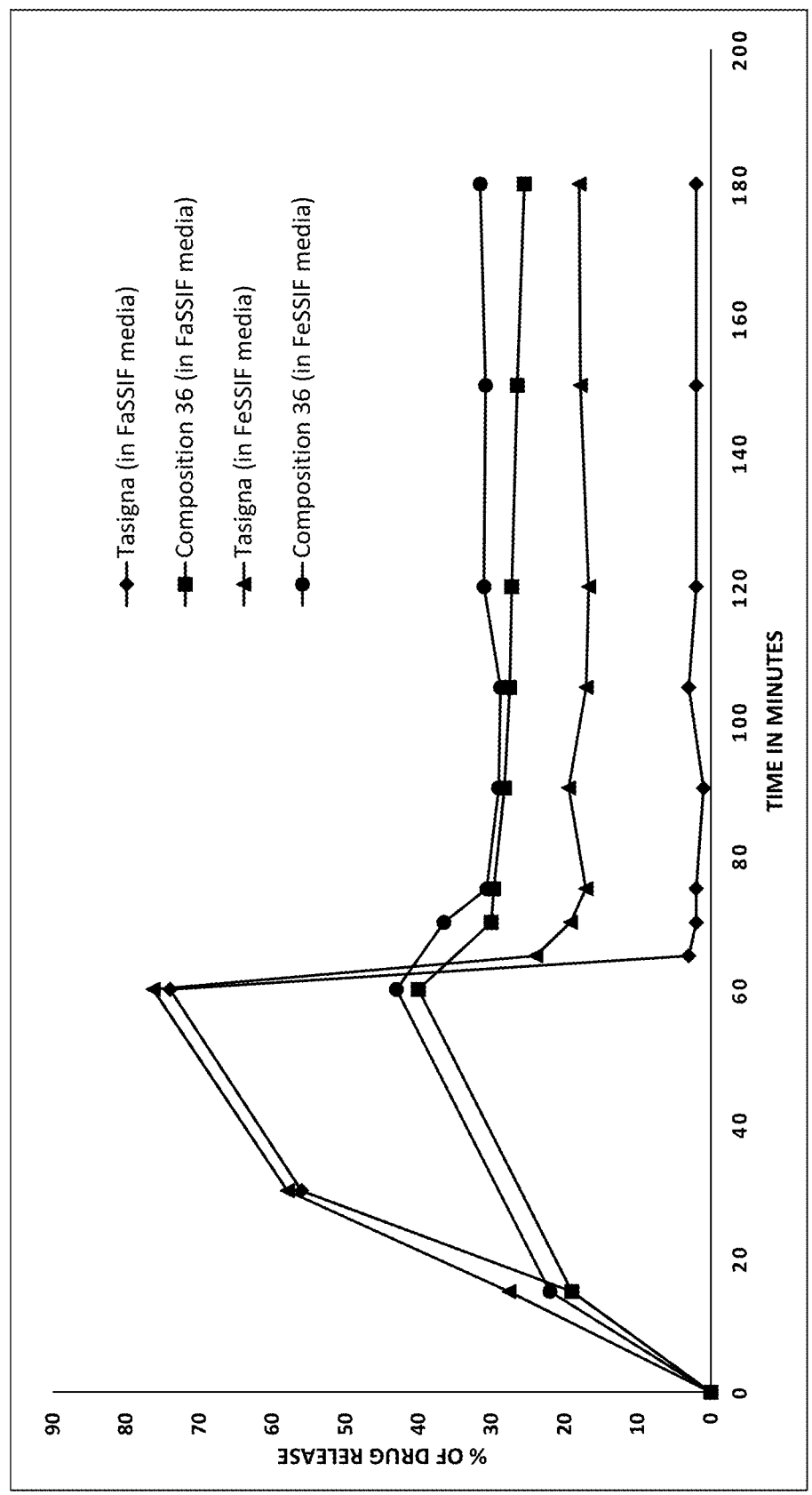
FIG. 5 illustrates comparative dissolution profiles of TASIGNA® 50 mg capsule and Composition 36 in 0.01 M HCl acid media followed by buffer media of FeSSIF or FaSSIF.

When TASIGNA® 50 mg capsule and Composition 36 are tested by using USP apparatus II (paddle); 500 mL of 0.01 M HCl media for 60 minutes and followed by 900 mL of FeSSIF media and FaSSIF media for 90 minutes at 37±0.5° C. and stirred at 75 rpm, the dissolution profile of Composition 36 was compared with TASIGNA®50 mg capsule in FeSSIF and FaSSIF media in following Table 12. Samples of 5 mL were withdrawn at 15, 30 and 60 minutes in 0.01 M HCl acid media and 65, 70, 75, 90, 105, 120, 150 and 180-minute time points in FeSSIF and FaSSIF media. Withdrawn samples were filtered with 0.45 μm nylon membrane filter and then diluted with dimethyl sulfoxide (DMSO) in 1:1 ratio and analysed using HPLC system with UV spectrophotometer at a wavelength 230 nm. The results of the measurements are given in Table 12 and shown graphically in FIG. 5.

Example 9

Solid dispersions of nilotinib fumarate were prepared, having the compositions set forth in Table 13

TABLE 13

| Ingredients | Composition | | | | | | |
|---|---|---|---|---|---|---|---|
| | 43 | 44 | 45 | 46 | 47 | 48 | 49 |
| | mg/unit | | | | | | |
| Nilotinib fumarate (solid dispersion from composition 7) | 243.0 | 218.7 | 170.2 | 121.5 | 218.7 | 170.2 | 121.5 |
| Nilotinib fumarate (solid dispersion from composition 10) | — | 24.3 | 72.9 | 121.5 | — | — | — |
| Nilotinib fumarate (solid dispersion from composition 12) | — | — | — | — | 24.3 | 72.9 | 121.5 |
| Microcrystalline cellulose | 89.2 | 89.2 | 89.2 | 89.2 | 89.2 | 89.2 | 89.2 |
| Croscarmellose Sodium | 17.7 | 17.7 | 17.7 | 17.7 | 17.7 | 17.7 | 17.7 |
| AEROSIL® | 1.8 | 1.8 | 1.8 | 1.8 | 1.8 | 1.8 | 1.8 |
| Magnesium stearate | 1.8 | 1.8 | 1.8 | 1.8 | 1.8 | 1.8 | 1.8 |
| Extra-granular material | | | | | | | |
| AEROSIL® | 1.8 | 1.8 | 1.8 | 1.8 | 1.8 | 1.8 | 1.8 |
| Magnesium stearate | 1.8 | 1.8 | 1.8 | 1.8 | 1.8 | 1.8 | 1.8 |
| Total | 357.2 | 357.2 | 357.2 | 357.2 | 357.2 | 357.2 | 357.2 |

The manufacturing procedure was as follows:
1. The required quantities of nilotinib fumarate solid dispersion of Composition 7, 10 and 12 were weighed and mixed with intragranular ingredients (i.e., microcrystal-

TABLE 12

| Dissolution media | Time in minutes | FaSSIF buffer media | | FeSSIF buffer media | |
|---|---|---|---|---|---|
| | | TASIGNA® 50 mg Capsule | Composition 36 | TASIGNA® 50 mg Capsule | Composition 36 |
| 0.01M HCl acid media | 0 | 0 | 0 | 0 | 0 |
| | 15 | 19 | 19 | 28 | 22 |
| | 30 | 56 | — | 58 | — |
| | 60 | 74 | 40 | 76 | 43 |
| Buffer media | 65 | 3 | — | 24 | — |
| | 70 | 2 | 30 | 19 | 36 |
| | 75 | 2 | 30 | 17 | 31 |
| | 90 | 1 | 28 | 19 | 29 |
| | 105 | 3 | 28 | 17 | 29 |
| | 120 | 2 | 27 | 17 | 31 |
| | 150 | 2 | 26 | 18 | 31 |
| | 180 | 2 | 26 | 18 | 32 | line cellulose, croscarmellose sodium, AEROSIL® and magnesium stearate) as mentioned in Table 13.
2. Mixtures obtained were compacted with roller compactor separately, these compacts were milled and passed through a 30-mesh screen separately. The obtained granules were blended with AEROSIL® to obtain pre-lubricated blends.
3. Pre-lubricated blends were lubricated with magnesium stearate.
4. Final blends were filled into capsules with respective fill weights for respective strengths of 25 mg to 100 mg.

Example 10

Nilotinib tartrate capsules were prepared, having the compositions set forth in Table 14.

TABLE 14

|  | Composition 50 | | Composition 51 | |
|---|---|---|---|---|
| Ingredients | mg/unit | % w/w | mg/unit | % w/w |
| Nilotinib tartrate (solid dispersion from composition 16) | 256 | 68.0 | — | — |
| Nilotinib tartrate (solid dispersion from composition 17) | — | — | 306 | 68.0 |
| Intra-granular Material | | | | |
| Microcrystalline cellulose | 78.55 | 25.0 | 93.9 | 25.0 |
| Croscarmellose Sodium | 15.64 | 5.0 | 18.65 | 5.0 |
| AEROSIL ® | 1.58 | 0.5 | 1.88 | 0.5 |
| Magnesium stearate | 1.58 | 0.5 | 1.88 | 0.5 |
| Extra-granular Material | | | | |
| AEROSIL ® | 1.58 | 0.5 | 1.88 | 0.5 |
| Magnesium stearate | 1.58 | 0.5 | 1.88 | 0.5 |
| Total | 356.48 | 100 | 426.07 | 100 |

Manufacturing Procedure:

The required quantities of nilotinib tartrate solid dispersion of Composition 16 and 17 were weighed according to Table 14, mixed with intragranular ingredients (i.e., microcrystalline cellulose, croscarmellose sodium, AEROSIL® and magnesium stearate) according to Table 14. The resulting mixtures obtained were each separately compacted with roller compactor. The resulting compacts were each separately milled and passed through a 30-mesh screen. The obtained granules were blended with AEROSIL® to obtain pre-lubricated blends. The pre-lubricated blends were lubricated with magnesium stearate. The final blends were filled into capsules with respective fill weights for respective strengths of 25 mg to 100 mg.

Dissolution Profiles of Composition 50 and 51 in 0.01M HCl Acid Media and Followed by FeSSIF Media of PH 5.0±0.05.

Figure 6:
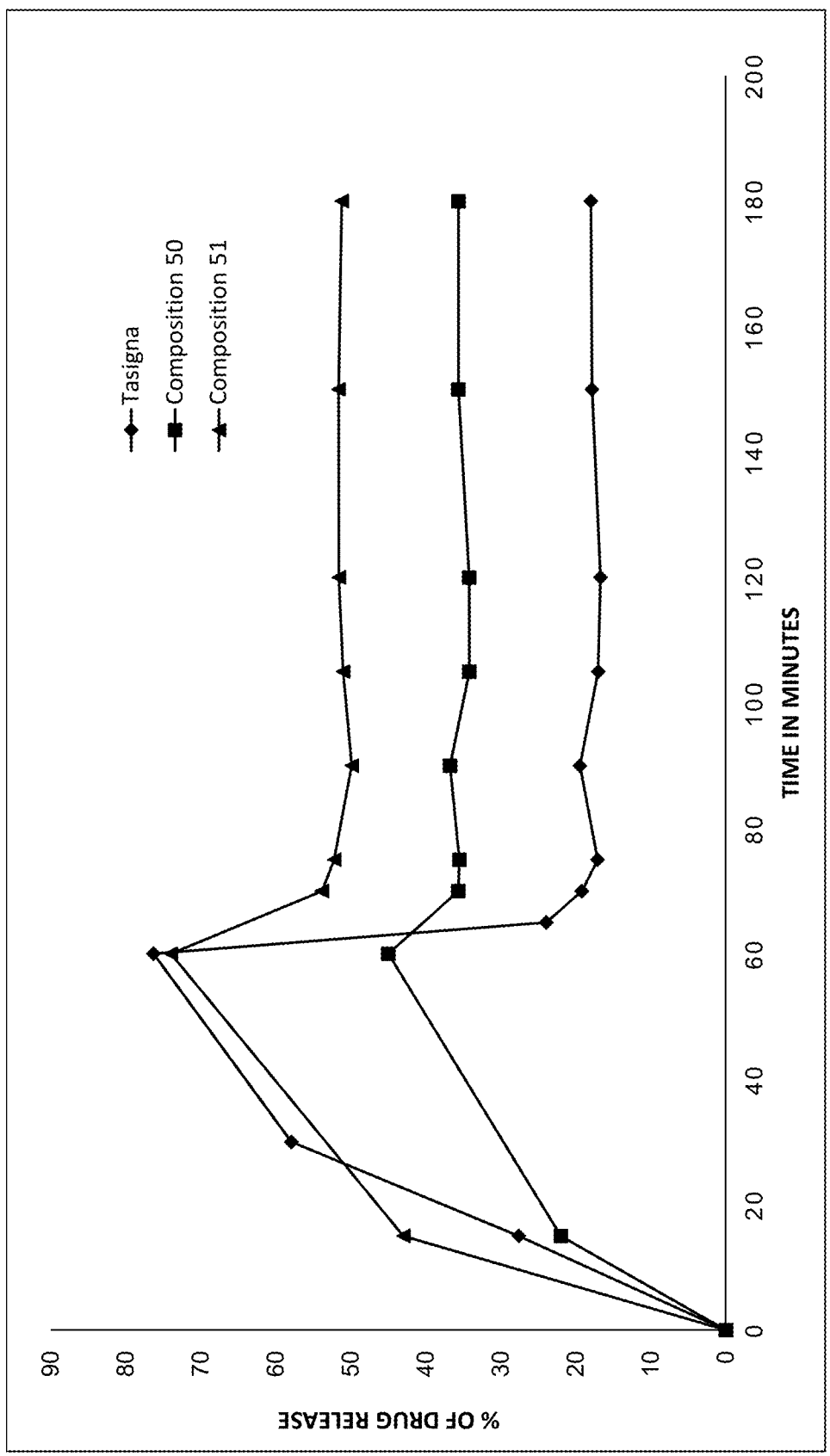
FIG. 6 illustrates comparative dissolution profiles of TASIGNA® 50 mg capsule and Composition 50 and 51 in 0.01 M HCl acid media followed by FeSSIF media of pH 5.0±0.05.

When tested by using USP apparatus II (paddle); 500 mL of 0.01 M HCl media for 60 minutes and followed by 900 mL of pH 5.0±0.05 FeSSIF media for 90 minutes at 37±0.5° C. and stirred at 75 rpm, the dissolution profiles of composition 50 and 51 were compared with TASIGNA® 50 mg capsule in following Table 15. Samples of 5 mL were withdrawn at 15, 30 and 60 minutes in 0.01 M HCl acid media and 65, 70, 75, 90, 105, 120, 150 and 180-minute time points in FeSSIF media. Withdrawn samples were filtered with 0.45 µm nylon membrane filter and then diluted with dimethyl sulfoxide (DMSO) in 1:1 ratio and analysed using HPLC system with UV spectrophotometer at a wavelength 230 nm. The results of the measurements are given in Table 15 and shown graphically in FIG. 6.

TABLE 15

|  |  | % of Drug released | | |
|---|---|---|---|---|
| Dissolution Media | Time (minutes) | TASIGNA ® 50 mg Capsule | Composition 50 | Composition 51 |
| 0.01M HCl acid media | 0 | 0 | 0 | 0 |
|  | 15 | 28 | 22 | 43 |
|  | 30 | 58 | — | — |
|  | 60 | 76 | 45 | 74 |
| FeSSIF buffer media | 65 | 24 | — | — |
|  | 70 | 19 | 36 | 54 |
|  | 75 | 17 | 36 | 52 |
|  | 90 | 19 | 37 | 50 |
|  | 105 | 17 | 34 | 51 |
|  | 120 | 17 | 34 | 52 |
|  | 150 | 18 | 36 | 52 |
|  | 180 | 18 | 36 | 51 |

Example 11

Solid dispersion of nilotinib tartrate was prepared, having the composition set forth in Table 16

TABLE 16

|  | Composition 52 | |
|---|---|---|
| Ingredients | mg/unit | % w/w |
| Nilotinib tartrate | 64 | 19.9 |
| HPMC-AS MF | 200 | 62.1 |
| Tartaric acid | 50 | 15.5 |
| AEROSIL ® | 5 | 1.6 |
| Magnesium stearate | 3 | 0.9 |
| Total | 322 | 100 |

Manufacturing Procedure:

The required quantities of nilotinib tartrate, HPMC-AS MF and tartaric acid were weighed and blended for 5 minutes to obtain a premix, according to Table 16. The premix obtained was subjected to hot-melt extrusion, which was performed on a hot melt extruder (Pharma 11 Twin-screw Extruder) at screw speed of 100 rpm using feed rate of 1 gram/minute. The extrude was collected at a temperature of 160° C., milled and passed through 40-mesh screen to obtain granules. The specified quantity of AEROSIL® was co-sifted with granules through 40-mesh screen and blended for 5 minutes to obtain pre-lubricated blend. Magnesium stearate was passed through 60-mesh screen and added to pre-lubricated blend and lubricated for 5 minutes.

Figure 7:
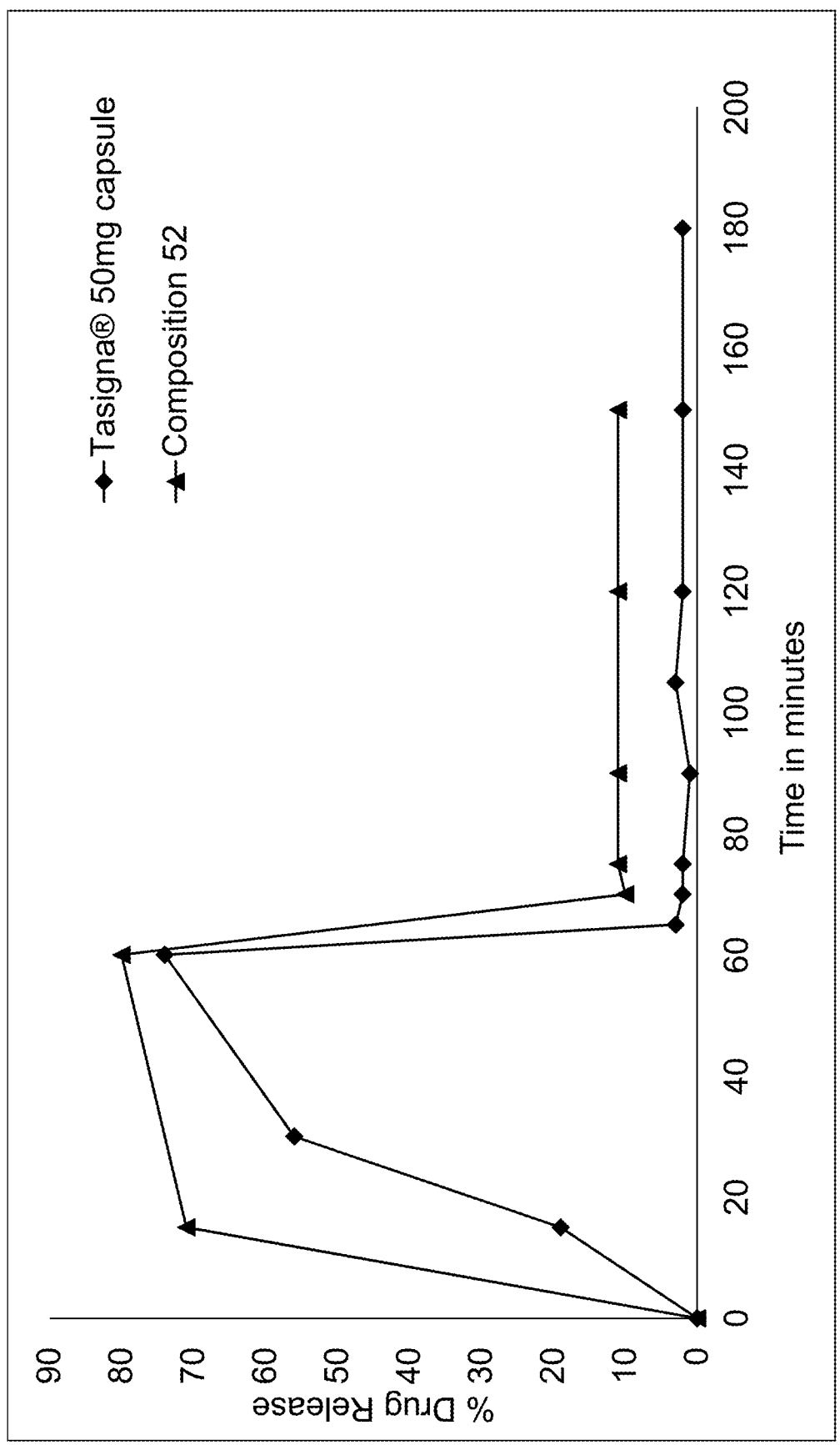
FIG. 7 illustrates comparative dissolution profile of TASIGNA® 50 mg capsule and Composition 52 in 0.01M HCl acid media and followed by double strength FaSSIF media.

Dissolution Profile of TASIGNA® 50 mg Capsule and Composition 52 in 0.01M HCl Acid Media and Followed by Double Strength FaSSIF Media When tested by using USP apparatus II (paddle); 500 mL of 0.01 M HCl media for 60 minutes and followed by 900 mL of double strength FaSSIF media for 120 minutes at 37±0.5° C. and stirred at 75 rpm, the dissolution profile of Composition 52 was compared with TASIGNA® 50 mg capsule in following Table 17. Samples of 5 mL were withdrawn at 15, 30 and 60 minutes in 0.01 M HCl acid media and 65, 70, 75, 90, 105, 120, 150 and 180-minute time points in FaSSIF media. Withdrawn samples were filtered with 0.45 µm nylon membrane filter and then diluted with dimethyl sulfoxide (DMSO) in 1:1 ratio and analysed using HPLC system with UV spectrophotometer at a wavelength 230 nm. The results of the measurements are given in Table 17 and shown graphically in FIG. 7.

TABLE 17

| Dissolution Media | Time (minutes) | % of Drug released | |
|---|---|---|---|
| | | TASIGNA® 50 mg Capsule | Composition 52 |
| 0.01M HCl acid media | 0 | 0 | 0 |
| | 15 | 19 | 71 |
| | 30 | 56 | — |
| | 60 | 74 | 80 |
| Double strength FaSSIF media | 65 | 3 | — |
| | 70 | 2 | 10 |
| | 75 | 2 | 11 |
| | 90 | 1 | 11 |
| | 105 | 3 | — |
| | 120 | 2 | 11 |
| | 150 | 2 | 11 |
| | 180 | 2 | — |

Example 12

A study was conducted to test the pharmacokinetics and bioavailability of a Composition 52 in healthy adult, beagle dog subjects, with the subjects in a fasted state.

This study is open label, balanced, non-randomized two-treatment, two-sequence, two-period, single-dose, two-way crossover oral bioequivalence study of Composition 52 and TASIGNA® 50 mg capsules was conducted in 8 healthy, adult, beagle dogs under fasting conditions (n=8).

TABLE 18

| Pharmacokinetic parameter | Composition 52 (Fast) | TASIGNA® (Fast) | Composition 52 (Fast)/ TASIGNA® (Fast) (%) | 90% Confidence interval (CI) |
|---|---|---|---|---|
| $C_{max}$ (ng/mL) | 783.4 ± 580.59 | 284.65 ± 138.9 | 255.48 | 148.59-439.28 |
| $AUC_{0-t}$ (ng · hr/mL) | 2497.25 ± 1518.22 | 901.76 ± 464.53 | 274.18 | 162.50-462.61 |
| $AUC_{0-\infty}$ (ng · hr/mL) | 2518.03 ± 1516.61 | 950.61 ± 465.20 | 257.3 | 159.43-415.26 |

Example 13

Nilotinib fumarate capsules were prepared, having the composition set forth in Table 19.

TABLE 19

| | Composition 53 | |
|---|---|---|
| Ingredients | mg/capsule | % w/w |
| Nilotinib fumarate | 60.77 | 20.7 |
| HPMC-AS MF | 182.3 | 62.2 |
| Fumaric acid | 50 | 17.1 |
| Methanol | 9000 | — |
| Total weight of solid dispersion filled in each capsule | 293.07 | 100 |

Manufacturing Procedure:

The required quantities of nilotinib fumarate, fumaric acid and HPMC-AS were dissolved in methanol solvent to prepare a solution containing 3% solid content. Prepared solution was sprayed on a spray dryer (Buchi B-290) at an inlet temperature of 115° C. and flow rate of 10 mL/minute. Obtained spray dried solid dispersion was filled into capsules.

Figure 8:
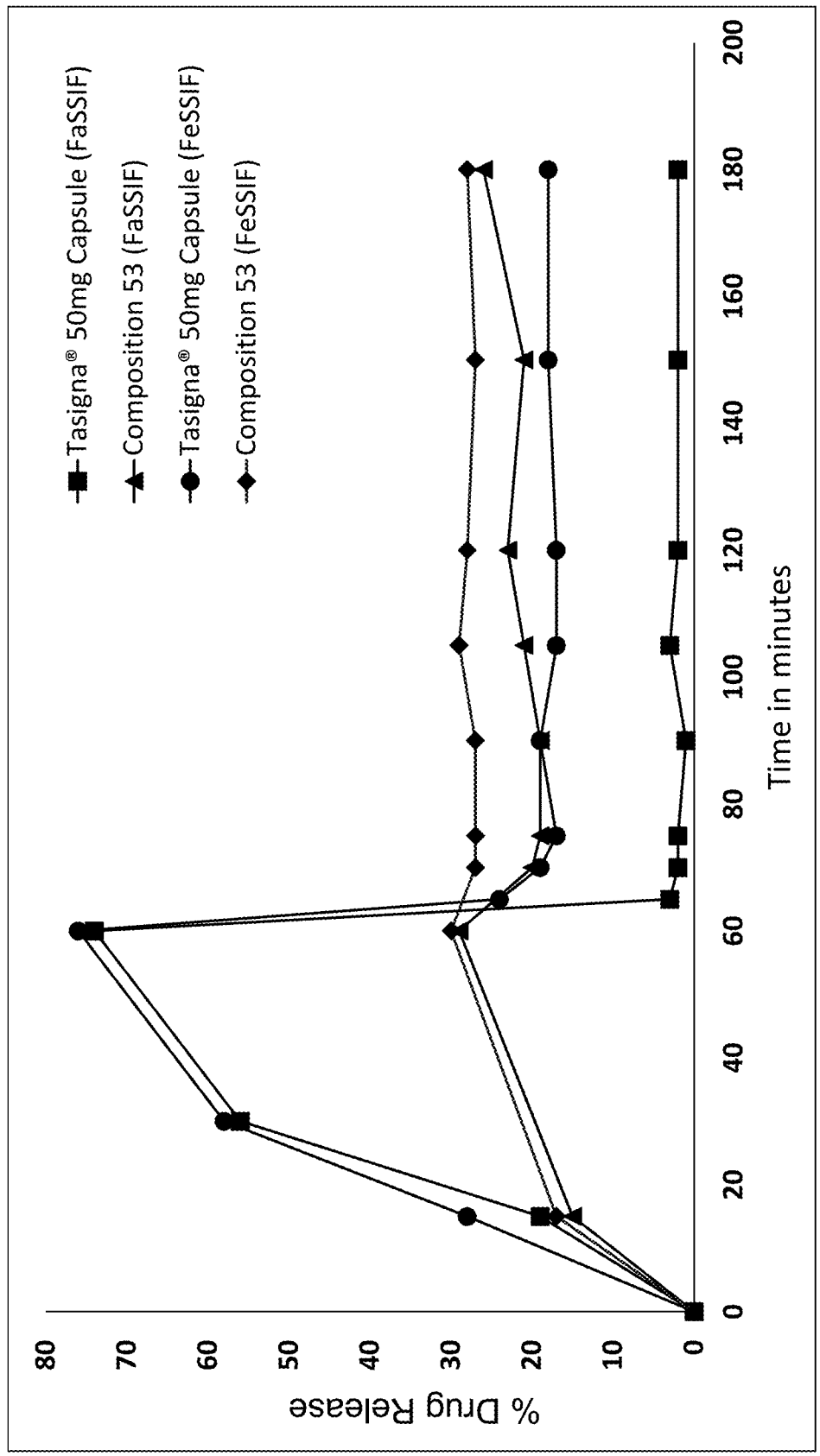
FIG. 8 illustrates comparative dissolution profiles of TASIGNA® 50 mg capsule and Composition 53 in 0.01M HCl acid media and followed by FaSSIF buffer media of pH 6.5±0.05 or followed by FeSSIF buffer media of pH 5.0±0.05.

Dissolution Profiles of TASIGNA® 50 mg Capsule and Composition 53 in 0.01M HCl Acid Media and Followed by pH 6.5 FaSSIF Buffer Media or Followed by pH 5.0 FeSSIF Buffer Media When tested by using USP apparatus II (paddle); 500 mL of 0.01 M HCl media for 60 minutes and followed by 900 mL of pH 6.5 FaSSIF buffer media or followed by pH 5.0 FeSSIF buffer media, each for 120 minutes at 37±0.5° C. and stirred at 75 rpm, the dissolution profiles of Composition 53 were compared with TASIGNA® 50 mg capsule in following Table 20. Samples of 5 mL were withdrawn at 15, 30 and 60 minutes in 0.01 M HCl acid media and 65, 70, 75, 90, 105, 120, 150 and 180-minute time points in FaSSIF buffer media and FeSSIF buffer media. Withdrawn samples were filtered with 0.45 μm nylon membrane filter and then diluted with dimethyl sulfoxide (DMSO) in 1:1 ratio and analysed using HPLC system with UV spectrophotometer at a wavelength 230 nm. The results of the measurements are given in Table 20 and shown graphically in FIG. 8.

TABLE 20

| Dissolution Media | Time (min) | % of Drug released | | | |
|---|---|---|---|---|---|
| | | FaSSIF buffer stage | | FeSSIF buffer stage | |
| | | TASIGNA® 50 mg Capsule | Composition 53 | TASIGNA® 50 mg Capsule | Composition 53 |
| 0.01M HCl acid media | 0 | 0 | 0 | 0 | 0 |
| | 15 | 19 | 15 | 28 | 17 |
| | 30 | 56 | — | 58 | — |
| | 60 | 74 | 29 | 76 | 30 |
| Buffer Stage | 65 | 3 | — | 24 | — |
| | 70 | 2 | 20 | 19 | 27 |
| | 75 | 2 | 19 | 17 | 27 |
| | 90 | 1 | 19 | 19 | 27 |
| | 105 | 3 | 21 | 17 | 29 |
| | 120 | 2 | 23 | 17 | 28 |
| | 150 | 2 | 21 | 18 | 27 |
| | 180 | 2 | 26 | 18 | 28 |

Example 14

A study was conducted to test the pharmacokinetics and bioavailability of a Composition 53 in 6 healthy adult beagle dog subjects, with the subjects in a fasted state.

TABLE 21

| Pharmacokinetic parameter | Composition 53 (Fast) | TASIGNA® (Fast) | Composition 53 (Fast)/TASIGNA® (Fast) (%) | 90% Confidence interval (CI) |
|---|---|---|---|---|
| $C_{max}$ (ng/mL) | 784.96 ± 1155.34 | 1142 ± 775.2 | 237.39 | 106.66-528.34 |
| $AUC_{0-t}$ (ng · hr/mL) | 2042.7 ± 2406.51 | 2538.53 ± 1875.4 | 218.51 | 111.48-428.29 |
| $AUC_{0-\infty}$ (ng · hr/mL) | 2110.8 ± 2425.08 | 3871.25 ± 2486.05 | 220.17 | 116.17-417.28 |

Example 15

A nilotinib fumarate tablets were prepared, having the composition set forth in Table 22.

TABLE 22

| | Composition 54 | | Composition 55 | |
|---|---|---|---|---|
| | Dry-granulation process | | Wet granulation process | |
| Ingredients | mg/tablet | % w/w | mg/tablet | % w/w |
| Nilotinib fumarate solid dispersion of Composition 53 | 293.07 | 57.6 | 293.07 | 57.9 |
| Intra-granular material | | | | |
| Microcrystalline cellulose | 100 | 19.6 | 100 | 19.8 |
| Crospovidone | 50 | 9.8 | — | — |
| AEROSIL® | 5 | 1.0 | — | — |
| Magnesium stearate | 3 | 0.6 | — | — |
| METHOCEL® E5 | — | — | 5 | 1.0 |
| Purified water | — | — | q.s. | — |
| Extra-granular material | | | | |
| Crospovidone | 50 | 9.8 | 100 | 19.8 |
| AEROSIL® | 5 | 1.0 | 5 | 1.0 |
| Magnesium stearate | 3 | 0.6 | 3 | 0.6 |
| Total | 509.07 | 100 | 506.07 | 100 |

Note:
q.s.—quantity sufficient

Manufacturing Procedure

The dry-granulation/slugging process comprised the following:
1. The required quantities of nilotinib fumarate solid dispersion of Composition 53, microcrystalline cellulose, Crospovidone, AEROSIL® and magnesium stearate as mentioned in Table 22 were weighed and blended for 5 minutes.
2. The obtained blend was compressed with 21.00 mm round punches to make slugs.
3. The obtained slugs were milled and passed through 40-mesh screen to obtain granules.

4. The required quantity of Crospovidone and AEROSIL® were weighed and co-sifted with granules through 40-mesh screen and blended for 5 minutes to obtain pre-lubricated blend.
5. Magnesium stearate was passed through 60-mesh screen and added to pre-lubricated blend and lubricated for 5 minutes.

The wet-granulation process comprised the following:
1. Nilotinib fumarate solid dispersion of Composition 53 was granulated with aqueous solution of METHOCEL® E5 in a rapid mixer granulator. The granules obtained were dried at 60° C. for 20 minutes. The dried granules were sifted through 40-mesh screen.
2. The required quantities of Crospovidone and AEROSIL® were weighed and co-sifted with granules through 40-mesh screen and blended for 5 minutes to obtain pre-lubricated blend.
3. Magnesium stearate was passed through 60-mesh screen and added to pre-lubricated blend and lubricated for 5 minutes.

TABLE 23

| Compression parameters | Composition 54 | Composition 55 |
| --- | --- | --- |
| Tooling | 11.00 mm round biconvex punches | 11.00 mm round biconvex punches |
| Hardness | 7-8 kp | 7-8 kp |
| Thickness | 6.4-6.5 mm | 6.4-6.5 mm |
| Disintegration time | NMT* 3 minutes | NMT* 3 minutes |

*NMT—Not More Than

Dissolution Profiles of TASIGNA® 50 mg Capsule, Composition 54 and 55 in 0.01N HCl Acid Media and Followed by PH 6.5 FaSSIF Buffer Media.

Figure 9:
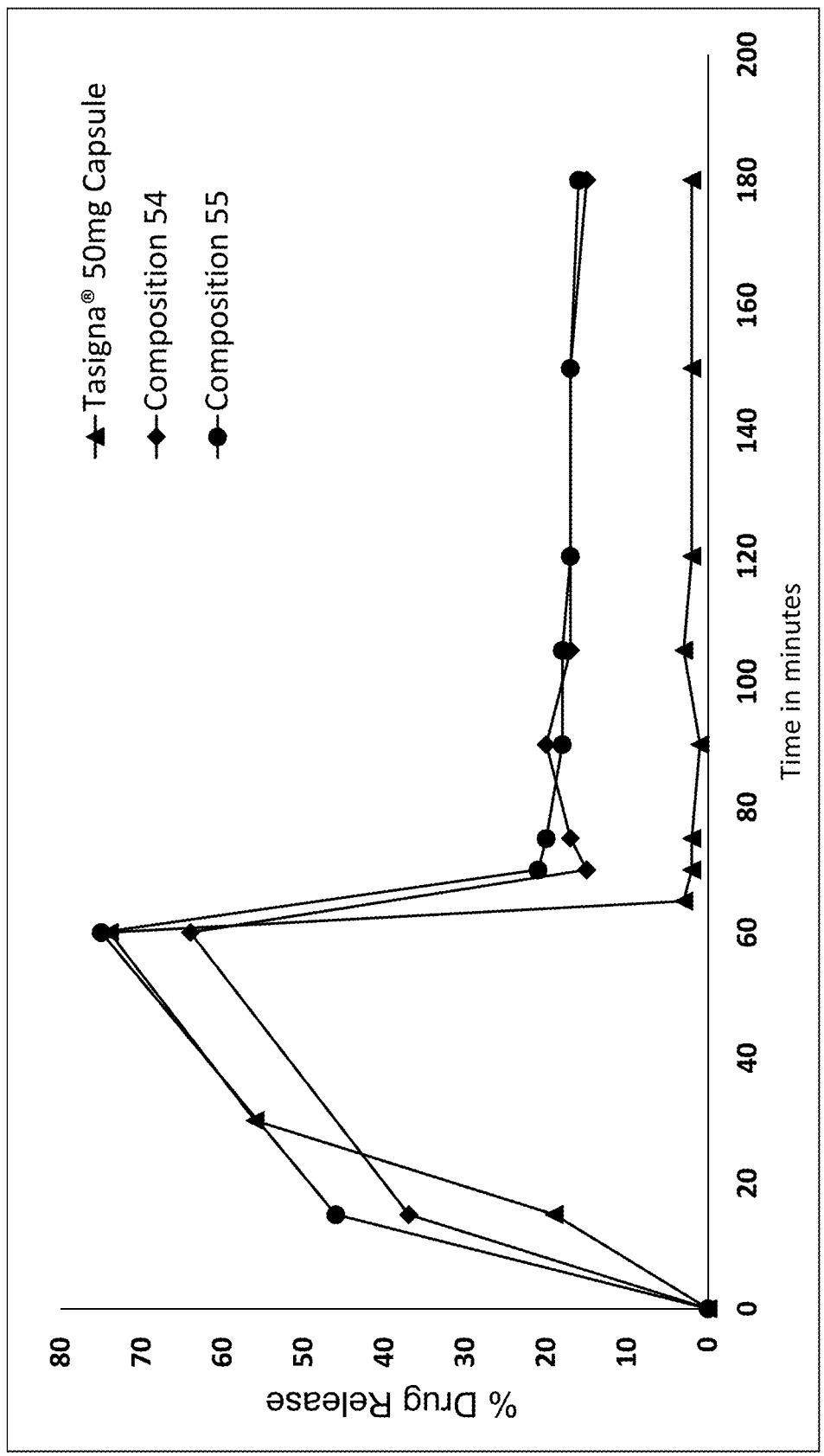
FIG. 9 illustrates comparative dissolution profiles of TASIGNA® 50 mg capsule, Composition 54 and 55 in 0.01N HCl acid media and followed by FaSSIF buffer media of pH 6.5±0.05.

When tested by using USP apparatus II (paddle); 500 mL of 0.01 N HCl media for 60 minutes and followed by 900 mL of pH 6.5 FaSSIF buffer media for 120 minutes at 37±0.5° C. and stirred at 75 rpm, the dissolution profiles of Composition 54 and 55 were compared with TASIGNA® 50 mg capsule in following Table 24. Samples of 5 mL were withdrawn at 15, 30 and 60 minutes in 0.01 N HCl acid media and 65, 70, 75, 90, 105, 120, 150 and 180-minute time points in FaSSIF buffer media. Withdrawn samples were filtered with 0.45 μm nylon membrane filter and then diluted with dimethyl sulfoxide (DMSO) in 1:1 ratio and analysed using HPLC system with UV spectrophotometer at a wavelength 230 nm. The results of the measurements are given in Table 24 and shown graphically in FIG. 9.

TABLE 24

| | | % of Drug released | | |
| --- | --- | --- | --- | --- |
| Dissolution Media | Time (minutes) | TASIGNA® 50 mg Capsule | Composition 54 | Composition 55 |
| 0.01N HCl acid media | 0 | 0 | 0 | 0 |
| | 15 | 19 | 37 | 46 |
| | 30 | 56 | — | — |
| | 60 | 74 | 64 | 75 |
| FaSSIF Buffer Stage | 65 | 3 | — | — |
| | 70 | 2 | 15 | 21 |
| | 75 | 2 | 17 | 20 |
| | 90 | 1 | 20 | 18 |
| | 105 | 3 | 17 | 18 |
| | 120 | 2 | 17 | 17 |
| | 150 | 2 | 17 | 17 |
| | 180 | 2 | 15 | 16 |

Example 16

Hot-Melt Extrusion Process Optimization

The process for the preparation of the pharmaceutical compositions of present invention involves an extrusion process followed by a formulation process. Formation of an impurity was observed and determined to be directly related to process temperature of hot-melt extrusion employed. Optimization of process temperature, feed rate and screw speed during hot-melt extrusion was critical in order to reduce formation of impurities. Critical process parameters such as feed rate and screw speed were also found to have a significant impact on critical product attributes of the solid dispersion such as amorphous nature of nilotinib in solid dispersion.

Impact of different process temperatures on impurity formation in nilotinib solid dispersion is given in below Table 25.

TABLE 25

| | | Known impurity | | | Unknown Impurity | | | | | |
| --- | --- | --- | --- | --- | --- | --- | --- | --- | --- | --- |
| | | Impurities | | | | | | | | |
| | | Impurity D | N-Oxide | NLT-C | UI*-1 | UI-2 | UI-3 | UI-4 | UI-5 | |
| | RRT** | 0.68 | 1.08 | 1.18 | 0.822 | 0.84 | 0.90 | 0.94 | 0.96 | PXRD |
| Process Temperature (° C.) | 160 | 0.04 | 0.01 | 0.04 | 0.03 | 0.04 | ND | 0.09 | 0.02 | Amorphous |
| | 170 | 0.04 | 0.02 | 0.04 | 0.03 | 0.06 | 0.01 | 0.14 | 0.02 | Amorphous |
| | 180 | 0.05 | 0.01 | 0.04 | 0.04 | 0.05 | ND | 0.16 | 0.01 | Amorphous |
| | 190 | 0.06 | 0.01 | 0.03 | 0.04 | 0.07 | ND | 0.24 | 0.03 | Amorphous |
| | 200 | 0.06 | 0.03 | 0.03 | 0.04 | 0.06 | ND | 0.19 | 0.03 | Amorphous |

*UI = Unknown Impurity;
**RRT = Relative Retention time

Impact of different feed rate and screw speed on impurity formation in nilotinib solid dispersion is given in below Table 26.

TABLE 26

| Feed Rate (g/min) | Screw Speed | Impurity D 0.68 | UI-1 0.82 | UI-2 0.84 | UI-3 0.9 | UI-4 0.94 | UI-5 0.96 | N-Oxide 1.08 | NLT-C 1.18 | PXRD |
|---|---|---|---|---|---|---|---|---|---|---|
| | | | | Impurities RRT % of Impurity | | | | | | |
| 3 | 325 | ND | ND | 0.03 | ND | 0.06 | ND | ND | ND | Amorphous |
| 4.6 | 325 | ND | ND | 0.02 | ND | 0.02 | ND | ND | ND | Amorphous |
| 4.6 | 250 | ND | ND | ND | ND | ND | ND | ND | ND | Crystalline |
| 4.6 | 200 | ND | ND | ND | ND | ND | ND | ND | ND | Crystalline |
| 4.6 | 150 | ND | ND | ND | ND | ND | ND | ND | ND | Crystalline |
| 4.6 | 100 | ND | ND | ND | ND | ND | ND | ND | ND | Crystalline |

*UI = Unknown Impurity;
RRT = Relative Retention time

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

While compositions and methods are described herein in terms of "comprising" various components or steps, the compositions and methods can also "consist essentially of" or "consist of" the various components and steps.

The invention claimed is:

1. A pharmaceutical composition comprising a therapeutically effective amount of an amorphous solid dispersion of nilotinib tartrate,
wherein a dosage of nilotinib administered in the pharmaceutical composition is reduced by at least about 50% w/w compared to a dosage of nilotinib administered in a reference formulation.

2. The pharmaceutical composition according to claim 1, wherein the dosage of nilotinib administered in a unit dosage form of the reference formulation is 150 mg.

3. The pharmaceutical composition according to claim 1, wherein the dosage of nilotinib administered in a unit dosage form of the reference formulation is 200 mg.

4. The pharmaceutical composition according to claim 1, wherein the amount of nilotinib in a unit dosage form of the pharmaceutical composition is about 75 mg.

5. The pharmaceutical composition according to claim 1, wherein the amount of nilotinib in a unit dosage form of the pharmaceutical composition is about 100 mg.

6. The pharmaceutical composition according to claim 1, wherein the amount of nilotinib in a unit dosage form of said composition is about 71 mg.

7. The pharmaceutical composition according to claim 1, wherein the amount of nilotinib in a unit dosage form of said composition is about 95 mg.

8. The pharmaceutical composition according to claim 1, wherein said pharmaceutical composition, after oral administration in a human subject under fasting conditions, provides a geometric mean area under the curve AUC0-t ranging from about 80% to about 125% of a geometric mean area under the curve AUC0-t of said reference formulation following oral administration in a human subject under fasting conditions.

9. The pharmaceutical composition according to claim 1, wherein said pharmaceutical composition, after oral administration under fasting conditions, is bioequivalent to the reference formulation, after oral administration under fasting conditions.

* * * * *